United States Patent
Mavro et al.

(10) Patent No.: US 7,238,212 B2
(45) Date of Patent: Jul. 3, 2007

(54) IMIDAZOLE COMPOUNDS AND USE OF THESE COMPOUNDS FOR DYEING KERATINOUS FIBERS

(75) Inventors: Jacqueline Mavro, Le Perreux (FR); Laurent Vidal, Paris (FR); Jean-Baptiste Saunier, Paris (FR)

(73) Assignee: L'Oreal, S.A., Paris (FR)

( * ) Notice: Subject to any disclaimer, the term of this patent is extended or adjusted under 35 U.S.C. 154(b) by 264 days.

(21) Appl. No.: 10/857,919

(22) Filed: Jun. 2, 2004

(65) Prior Publication Data

US 2005/0011019 A1 Jan. 20, 2005

Related U.S. Application Data

(60) Provisional application No. 60/513,570, filed on Oct. 24, 2003.

(30) Foreign Application Priority Data

Jun. 2, 2003 (FR) .................. 03 06621

(51) Int. Cl.
*A61K 7/13* (2006.01)
(52) U.S. Cl. .............. 8/405; 8/406; 8/409; 8/410; 8/412; 8/414; 8/570; 548/335.1; 548/341.1
(58) Field of Classification Search ............ 8/405, 8/406, 409, 410, 414, 412, 570; 548/335.1, 548/341.1
See application file for complete search history.

(56) References Cited

U.S. PATENT DOCUMENTS

| 5,294,709 A | * | 3/1994 | Ukai et al. .................. 544/263 |
| 6,638,321 B1 | | 10/2003 | Genet et al. |
| 2003/0092754 A1 | * | 5/2003 | Nishimuta et al. .......... 514/398 |

FOREIGN PATENT DOCUMENTS

| DE | 39 29 173 | 3/1991 |
| DE | 100 38 029 | 2/2002 |
| EP | 0 396 427 | 11/1990 |
| FR | 2 766 178 | 1/1999 |
| WO | WO 01/66646 | 9/2001 |
| WO | WO 02/39970 | 5/2002 |

OTHER PUBLICATIONS

English language Derwent Abstract of DE 39 29 173, Mar. 7, 1991.
English language Derwent Abstract of DE 100 38 029, Feb. 14, 2002.

* cited by examiner

*Primary Examiner*—Eisa Elhilo
(74) *Attorney, Agent, or Firm*—Finnegan, Henderson, Farabow, Garrett & Dunner LLP

(57) ABSTRACT

The disclosure relates to novel imidazole compounds which can be useful as couplers for the oxidation dyeing of keratinous fibers. The present disclosure also relates to a dyeing composition for dyeing keratinous fibers comprising at least one oxidation base and at least one coupler of the imidazole type as disclosed herein, and the dyeing method using this composition.

30 Claims, No Drawings

IMIDAZOLE COMPOUNDS AND USE OF THESE COMPOUNDS FOR DYEING KERATINOUS FIBERS

This application claims benefit of U.S. Provisional Application No. 60/513,570, filed Oct. 24, 2003, which is herein incorporated by reference.

The present disclosure relates to novel compounds of the imidazole type which can be useful as couplers for the oxidation dyeing of keratinous fibers.

It is known to dye keratinous fibers, such as human hair, with dyeing compositions containing oxidation dye precursors, for instance ortho- or para-phenylenediamines, ortho- or para-aminophenols, heterocyclic compounds such as diaminopyrazole derivatives, pyrazolo[1,5-a]pyrimidine derivatives, pyrimidine derivatives, pyridine derivatives, 5,6-dihydroxyindole derivatives, and 5,6-dihydroxyindoline derivatives. Oxidation dye precursors, also called oxidation bases, are colorless or weakly colored compounds which, when combined with oxidizing products, can give rise, by a process of oxidative condensation, to colored and coloring compounds.

It is also known that the shades obtained with these oxidation bases can be varied by combining them with couplers or color modifiers. The color modifiers may be chosen from, for example, meta-phenylenediamines, meta-aminophenols, meta-hydroxyphenols and certain heterocyclic compounds such as, for example, pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules used in oxidation bases and couplers makes it possible to obtain a rich palette of colors.

The so-called "permanent" color obtained using oxidation dyes should, moreover, be able to meet a number of requirements. For example, the dyes should be without toxicological drawbacks, they can make it possible to obtain shades in the desired intensity and can exhibit good resistance to external agents such as light, adverse weather conditions, washing, permanent waving, perspiration, and rubbing.

The dyes can also make it possible to cover grey hair, and be the least selective possible, that is to say the dyes can make it possible to obtain the smallest possible differences in color along the same keratinous fiber, which may be differently sensitised, i.e. damaged, between its tip and its root. They may also exhibit good chemical stability in the formulations.

Thus, it is desirable to provide novel couplers that make it possible to obtain a range of shades even more varied, and dyeing compositions which comprise dyes that can be powerful, uniform between the root and tip of the hair, can have good chromaticity, which can be scarcely selective and can be particularly resistant, while being capable of generating intense colorations in varied shades, such as in the basic shades.

Accordingly, one aspect of the present disclosure is a compound of the imidazole type of formula (I) and its addition salts with an acid or a base:

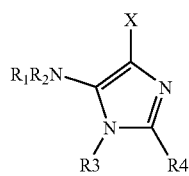

(I)

wherein:
$R_1$, $R_2$ and $R_4$, which may be identical or different, are chosen from
hydrogen atoms;
phenyl radicals optionally substituted with at least one entity chosen from halogen atoms, and hydroxyl, $C_1$–$C_4$ alkoxy, carboxyl, carboxamido, $(C_1$–$C_4)$alkylsulphonyl (—$SO_2$alkyl), sulphonic (—$SO_3H$), alkylsulphoxide (—SO-alkyl), alkylsulphonamido (($C_1$–$C_4$)alkyl$SO_2NH$—), $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals;
linear and branched $C_1$–$C_8$ alkyl radicals optionally substituted with at least one radical chosen from hydroxyl, $C_1$–$C_2$ alkoxy, carboxyl, carboxamido, $(C_1$–$C_4)$alkylsulphonyl, sulphonic, alkylsulphoxide, alkylsulphonamido and $NR_{13}R_{14}$ radicals,
$R_4$ may also be chosen from:
$NR_{22}R_{23}$ radicals where $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals,
5- and 6-membered aromatic heterocycles optionally substituted with at least one radical chosen from hydroxyl, $C_1$–$C_2$ alkoxy, amino, dimethylamino, 2-hydroxyethylamino, bis(2-hydroxyethyl)amino and chlorine radicals,
$R_1$ and $R_2$ may also form with the nitrogen atom to which they are attached a 5- to 8-membered heterocycle in which at least one carbon atom of the carbon ring may be replaced by an entity chosen from oxygen, nitrogen and sulphur atoms, and $SO_2$ groups; wherein the carbon atoms of the ring may be substituted with a radical $R_5$; and with the proviso that the ring does not comprise a peroxide bond, or diazo or nitroso radicals;
$R_5$ is chosen from:
halogen atoms;
$C_1$–$C_4$ alkyl radicals optionally substituted with at least one radical chosen from hydroxyl, carboxyl, $C_1$–$C_4$ alkoxycarbonyl, $C_1$–$C_4$ alkoxy and $NR_6R_7$ radicals;
carboxyl radicals;
carboxamido (alkylCONH—) radicals;
$(C_1$–$C_4)$alkylsulphonyl (—$SO_2$alkyl) radicals;
alkylsulphonamido (($C_1$–$C_4$)alkyl$SO_2NH$—) radicals;
hydroxyl radicals;
$C_1$–$C_4$ alkoxy radicals;
$C_2$–$C_4$ hydroxyalkoxy radicals;
aminosulphonyl ($NH_2$—$SO_2$—) radicals;
$C_1$–$C_4$ thioether radicals;
$(C_1$–$C_4)$alkylsulphoxide (—SOalkyl) radicals;
$(C_1$–$C_4)$alkylsulphonyl (—$SO_2$alkyl) radicals; and
$NR_8R_9$ radicals;
$R_3$ is chosen from
hydrogen atoms;
$(C_1$–$C_4)$alkylsulphonyl (—$SO_2$alkyl) radicals;
linear and branched $C_1$–$C_8$ alkyl radicals substituted with at least one radical chosen from hydroxyl, $OR_{10}$, carboxyl, carboxamido, $(C_1$–$C_4)$alkylsulphonyl, sulphonic (—$SO_3H$), $(C_1$–$C_4)$alkylsulphoxide (—SOalkyl), alkylsulphonamido (($C_1$–$C_4$)alkyl$SO_2NH$—) and $NR_{11}R_{12}$ radicals;
phenyl radicals and 5- and 6-membered aromatic heterocycles, these radicals being optionally substituted with at least one entity chosen from halogens, and hydroxyl, $C_1$–$C_4$ alkoxy, carboxyl, carboxamido, $(C_1$–$C_4)$alkylsulphonyl, sulphonic (—$SO_3H$), alkylsulphoxide, $C_1$–$C_4$ thioether, alkylsulphonamido $((C_1$–$C_4)$ alkylSO$_2$NH—), $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals;

$R_{10}$ is chosen from $C_1$–$C_4$ alkyl radicals optionally substituted with at least one radical chosen from hydroxyl, $C_1$–$C_2$ alkoxy, amino, (di)($C_1$–$C_4$)alkylamino and $C_2$–$C_4$ (poly)hydroxyalkylamino radicals, $R_6$, $R_7$, $R_8$, $R_9$, $R_{11}$, $R_{12}$, $R_{13}$, $R_{14}$, which are identical or different, are chosen from hydrogen atoms, acyl radicals, carboxamido radicals, $C_1$–$C_4$ alkyl radicals optionally substituted with at least one radical chosen from hydroxyl, $C_1$–$C_4$ alkoxy, sulphino, $(C_1$–$C_4)$alkylsulphonyl, alkylsulphonamido, carboxyl, carboxamido, alkylsulphoxide, amino, mono- and di($C_1$–$C_4$)alkylamino and $C_2$–$C_4$ (poly)hydroxyalkylamino radicals;

$R_{11}$ and $R_{12}$ may also form with the nitrogen atom carrying them a 5- to 8-membered ring optionally substituted with at least one entity chosen from halogens, and hydroxyl, $C_1$–$C_4$ alkoxy, carboxyl, carbamyl, $(C_1$–$C_4)$alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from the radicals hydroxyl, $C_1$–$C_4$ alkoxy, carboxyl, carboxamido, $(C_1$–$C_4)$ alkylsulphonyl, sulphonic, alkylsulphoxide, alkylsulphonamido and $NR_{13}R_{14}$ radicals, X is chosen from hydrogen atoms; halogen atoms; $C_1$–$C_4$ alkoxy radicals; phenoxy radicals optionally substituted with at least one entity chosen from halogens, hydroxyl, $C_1$–$C_4$ alkoxy, carboxyl, $C_1$–$C_4$ alkoxycarbonyl, carboxamido, sulphino, $(C_1$–$C_4)$alkylsulphonyl, sulphonic, alkylsulphoxide, $C_1$–$C_4$ thioether, alkylsulphonamido, $NR_{13}R_{14}$, and $C_1$–$C_4$ alkyl radicals; and $C_1$–$C_4$ thioether radicals optionally substituted with hydroxyl, $C_1$–$C_2$ alkoxy, carboxyl, and sulphonic radicals.

The imidazole compounds of of formula (I) as disclosed herein are suitable not only for use as coupler for the oxidation dyeing of keratinous fibers, but in addition may lead to intense colorations with low selectivity. These compounds also make it possible to obtain dyeing compositions leading to colorations which can be quite resistant to the various attacks to which hair may be subjected, such as light, adverse weather conditions, washing, and perspiration. The oxidation dyeing compositions in accordance with the present disclosure make it possible furthermore to obtain shades in a very broad palette of colors.

Another aspect of the present disclosure is a dyeing composition comprising,
at least one oxidation base, and
at least one coupler of the imidazole type of formula (I) as defined above.

Still another aspect of the present disclosure is a dyeing method using the compositions disclosed herein.

Yet another aspect of the present disclosure is the use of the compounds of formula (I) for the oxidation dyeing of keratinous fibers, for instance, human keratinous fibers such as the hair.

In the context of the present disclosure, the expression "branched hydrocarbon chain" is understood to mean a chain that can form at least one 3- to 8-membered carbon rings. As used herein, the expression "unsaturated hydrocarbon chain" is understood to mean a chain that may comprise at least one double bond and/or at least one triple bond, it being possible for this hydrocarbon chain to lead to aromatic groups.

By way of non-limiting example, there may be mentioned for the radicals $R_1$ and $R_2$ of formula (I): hydrogen atoms, and methyl, ethyl, (iso)propyl, 2-hydroxyethyl, 1-hydroxyethyl, 2-carboxyethyl, 2-aminoethyl, 2-(dimethylamino) ethyl, 2-(acylamino)ethyl, 2-methoxyethyl, 1,2-dihydroxyethyl, 1-hydroxy-2-aminoethyl, 2-hydroxy-1-aminoethyl, acetyl, $NH_2$—CO—, dimethylcarboxamido, methylsulphonyl and phenyl radicals. For example, $R_1$ and $R_2$, which may be identical or different, can be chosen from hydrogen atoms, and methyl, 2-hydroxyethyl, 2-carboxyethyl and 1,2-dihydroxyethyl radicals.

According to one embodiment of the present disclosure, $R_1$ and $R_2$, which may be identical or different, may be chosen from:
hydrogen atoms;
phenyl radicals optionally substituted with at least one radical chosen from hydroxyl, $C_1$–$C_4$ alkoxy, carboxamido, alkylsulphoxide, alkylsulphonamido, $N_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxamido, alkylsulphonamido and $NR_{13}R_{14}$ radicals;
linear and branched $C_1$–$C_6$ alkyl radicals optionally substituted with at least one radical chosen from hydroxyl, $C_1$–$C_2$ alkoxy, carboxyl, carboxamido, $(C_1$–$C_4)$alkylsulphonyl, sulphonic, alkylsulphoxide, alkylsulphonamido and $NR_{13}R_{14}$ radicals.

According to another embodiment disclosed herein, $R_1$ and $R_2$, which may be identical or different, may be chosen from hydrogen atoms; phenyl radicals; linear and branched $C_1$–$C_4$ alkyl radicals substituted with at least one radical chosen from hydroxyl, $C_1$–$C_2$ alkoxy, amino, di($C_1$–$C_4$) alkylamino, carboxyl, carboxamido, alkylsulphonamido, and $NR_{13}R_{14}$ radicals, wherein $R_{13}$ and $R_{14}$, which can be identical or different, are chosen from hydrogen atoms, acyl, and $C_1$–$C_2$ alkyl radicals, wherein the $C_1$–$C_2$ alkyl radicals are optionally substituted with hydroxyl, and $C_1$–$C_2$ alkoxy radicals.

According to yet another embodiment of the present disclosure, $R_1$ and $R_2$ may form with the nitrogen atom to which they are attached a 5- to 8-membered heterocycle chosen from pyrrolidine, piperidine, homopiperidine, piperazine, and homopiperazine radicals, it being possible for the rings to be substituted with at least one $R_5$ radical.

By way of non-limiting example of this embodiment, $R_1$ and $R_2$ may form together with the nitrogen atom to which they are attached a heterocycle chosen from 2,5-dimethylpyrrolidine, proline, 3-hydroxyproline, 4-hydroxyproline, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 4-amino-3-hydroxypyrrolidine, 3-hydroxy-4-(2-hydroxyethyl)aminopyrrolidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-β-hydroxyethylhomopiperazine and the addition salts thereof.

For further example, $R_1$ and $R_2$ may form together with the nitrogen atom to which they are attached a heterocycle chosen from pyrrolidine, 3-hydroxypyrrolidine, 3-aminopyrrolidine, proline, 3-hydroxyproline, piperidine, 3- and 4-hydroxypiperidine, homopiperidine, homopiperazine, N-methylhomopiperazine, N-β-hydroxyethylhomopiperazine and the addition salts thereof.

By way of another example, non-limiting mention may be made of $R_3$ being chosen from hydrogen atoms, and methyl, ethyl, (iso)propyl, 2-hydroxyethyl, 1-hydroxyethyl, 2-carboxyethyl, 2-aminoethyl, 2-(dimethylamino)ethyl, 2-(acylamino)ethyl, 2-methoxyethyl, 1,2-dihydroxyethyl, 1-hydroxy-2-aminoethyl, 2-hydroxy-1-aminoethyl, methylsulphonyl and phenyl radicals. For instance, $R_3$ may be chosen from hydrogen atoms, and methyl, 2-hydroxyethyl, 2-carboxyethyl, 1,2-dihydroxyethyl, and phenyl radicals.

According to another embodiment of the present disclosure, $R_3$ may be chosen from hydrogen atoms, alkyl radicals, hydroxyalkyl radicals, alkylsulphonyl radicals, and phenyl radicals.

By way of example, non-limiting mention may be made of $R_4$ being chosen from methyl, ethyl, isopropyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 2-hydroxy-1-aminoethyl, amino, methylamino, dimethylamino, 2-hydroxyethylamino, bis(2-hydroxyethyl)amino, phenyl, 4-aminophenyl, 4-hydroxyphenyl, 4-dimethylaminophenyl, and 4-methoxyphenyl radicals.

According to another embodiment of the present disclosure, $R_4$ may be chosen from a hydrogen atom; amino radicals; sulphonic radicals; sulphoxide radicals; sulphonylamino radicals; linear and branched $C_1$–$C_6$ alkyl radicals optionally substituted with at least one radical chosen from hydroxyl, $C_1$–$C_2$ alkoxy, amino, carboxyl, carboxamido, and alkylsulphonamido radicals; $NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with hydroxyl and $C_1$–$C_2$ alkoxy radicals; phenyl radicals; and 5- and 6-membered aromatic heterocycles optionally substituted with at least one entity chosen from hydroxyl, $C_1$–$C_2$ alkoxy, amino, (di-)methylamino, 2-hydroxyethylamino, and bis(2-hydroxyethyl) amino radicals, and chlorine atoms.

For instance, $R_4$ may be chosen from a hydrogen atom, optionally substituted alkyl radicals, $NR_{22}R_{23}$ radicals, and phenyl radicals. According to one embodiment, $R_4$ may be chosen from hydrogen atoms, and methyl, hydroxymethyl, 2-hydroxyethyl, 1,2-dihydroxyethyl, amino, 2-hydroxyethylamino and phenyl radicals.

According to another embodiment, $R_4$ may be chosen from a hydrogen atom and alkyl radicals.

In formula (I) above, X may be chosen from a hydrogen atom, halogen atoms such as chlorine, and alkoxy radicals, for example, methoxy.

Among the compounds of formula (I) that may be used, non-limiting mention may be made of the following compounds, for example:
5-aminoimidazole,
5-amino-2-methylimidazole,
5-amino-2-phenylimidazole,
5-amino-N-methylimidazole,
5-amino-2-methyl-N-methylimidazole,
5-amino-2-phenyl-N-methylimidazole,
5-amino-N-(2-hydroxyeth-1-yl)imidazole,
5-amino-2-methyl-N-(2-hydroxyeth-1-yl)imidazole,
5-amino-2-phenyl-N-(2-hydroxyeth-1-yl)imidazole,
5-amino-N-(phenyl)imidazole,
5-amino-2-methyl-N-(phenyl)imidazole,
5-amino-2-phenyl-N-(phenyl)imidazole,
5-methylaminoimidazole,
5-methylamino-2-methylimidazole,
5-methylamino-2-phenylimidazole,
5-methylamino-N-methylimidazole,
5-methylamino-2-methyl-N-methylimidazole,
5-methylamino-2-phenyl-N-methylimidazole,
5-methylamino-N-(2-hydroxyeth-1-yl)imidazole,
5-methylamino-2-methyl-N-(2-hydroxyeth-1-yl)imidazole,
5-methylamino-2-phenyl-N-(2-hydroxyeth-1-yl)imidazole,
5-methylamino-N-(phenyl)imidazole,
5-methylamino-2-methyl-N-(phenyl)imidazole,
5-methylamino-2-phenyl-N-(phenyl)imidazole,
5-dimethylaminoimidazole,
5-dimethylamino-2-methylimidazole,
5-dimethylamino-2-phenylimidazole,
5-dimethylamino-N-methylimidazole,
5-dimethylamino-2-methyl-N-methylimidazole,
5-dimethylamino-2-phenyl-N-methylimidazole,
5-dimethylamino-N-(2-hydroxyeth-1-yl)imidazole,
5-dimethylamino-2-methyl-N-(2-hydroxyeth-1-yl)imidazole,
5-dimethylamino-2-phenyl-N-(2-hydroxyeth-1-yl)imidazole,
5-dimethylamino-N-(phenyl)imidazole,
5-dimethylamino-2-methyl-N-(phenyl)imidazole,
5-dimethylamino-2-phenyl-N-(phenyl)imidazole,
5-(pyrrolidin-1-yl)imidazole,
5-(pyrrolidin-1-yl)-2-methylimidazole,
5-(pyrrolidin-1-yl)-2-phenylimidazole,
5-(pyrrolidin-1-yl)-N-methylimidazole,
5-(pyrrolidin-1-yl)-2-methyl-N-methylimidazole,
5-(pyrrolidin-1-yl)-2-phenyl-N-methylimidazole,
5-(pyrrolidin-1-yl)-N-(2-hydroxyeth-1-yl)imidazole,
5-(pyrrolidin-1-yl)-2-methyl-N-(2-hydroxyeth-1-yl)imidazole,
5-(pyrrolidin-1-yl)-2-phenyl-N-(2-hydroxyeth-1-yl)imidazole,
5-(pyrrolidin-1-yl)-N-(phenyl)imidazole,
5-(pyrrolidin-1-yl)-2-methyl-N-(phenyl)imidazole,
5-(pyrrolidin-1-yl)-2-phenyl-N-(phenyl)imidazole,
5-(3-hydroxypyrrolidin-1-yl)imidazole,
5-(3-hydroxypyrrolidin-1-yl)-2-methylimidazole,
5-(3-hydroxypyrrolidin-1-yl)-2-phenylimidazole,
5-(3-hydroxypyrrolidin-1-yl)-N-methylimidazole,
5-(3-hydroxypyrrolidin-1-yl)-2-methyl-N-methylimidazole,
5-(3-hydroxypyrrolidin-1-yl)-2-phenyl-N-methylimidazole,
5-(3-hydroxypyrrolidin-1-yl)-N-(2-hydroxyeth-1-yl)imidazole,
5-(3-hydroxypyrrolidin-1-yl)-2-methyl-N-(2-hydroxyeth-1-yl)imidazole,
5-(3-hydroxypyrrolidin-1-yl)-2-phenyl-N-(2-hydroxyeth-1-yl)imidazole,
5-(3-hydroxypyrrolidin-1-yl)-N-(phenyl)imidazole,
5-(3-hydroxypyrrolidin-1-yl)-2-methyl-N-(phenyl)imidazole,
5-(3-hydroxypyrrolidin-1-yl)-2-phenyl-N-(phenyl)imidazole,
5-(piperidin-1-yl)imidazole,
5-(piperidin-1-yl)-2-methylimidazole,
5-(piperidin-1-yl)-2-phenylimidazole,
5-(piperidin-1-yl)-N-methylimidazole, 5-(piperidin-1-yl)-2-methyl-N-methylimidazole,
5-(piperidin-1-yl)-2-phenyl-N-methylimidazole,
5-(piperidin-1-yl)-N-(2-hydroxyeth-1-yl)imidazole,
5-(piperidin-1-yl)-2-methyl-N-(2-hydroxyeth-1-yl)imidazole,
5-(piperidin-1-yl)-2-phenyl-N-(2-hydroxyeth-1-yl)imidazole,
5-(piperidin-1-yl)-N-(phenyl)imidazole,
5-(piperidin-1-yl)-2-methyl-N-(phenyl)imidazole,
5-(piperidin-1-yl)-2-phenyl-N-(phenyl)imidazole,
5-(2-hydroxyethyl)aminoimidazole,
5-(2-hydroxyethyl)amino-2-methylimidazole,
5-(2-hydroxyethyl)amino-2-phenylimidazole,
5-(2-hydroxyethyl)amino-N-methylimidazole,
5-(2-hydroxyethyl)amino-2-methyl-N-methylimidazole,
5-(2-hydroxyethyl)amino-2-phenyl-N-methylimidazole,
5-(2-hydroxyethyl)amino-N-(2-hydroxyeth-1-yl)imidazole,
5-(2-hydroxyethyl)amino-2-methyl-N-(2-hydroxyeth-1-yl)imidazole,
5-(2-hydroxyethyl)amino-2-phenyl-N-(2-hydroxyeth-1-yl)imidazole,
5-(2-hydroxyethyl)amino-N-(phenyl)imidazole,
5-(2-hydroxyethyl)amino-2-methyl-N-(phenyl)imidazole,
5-(2-hydroxyethyl)amino-2-phenyl-N-(phenyl)imidazole,
5-amino-4-chloroimidazole,
5-amino-2-methyl-4-chloroimidazole,
5-amino-2-phenyl-4-chloroimidazole,
5-amino-N-methyl-4-chloroimidazole,
5-amino-2-methyl-N-methyl-4-chloroimidazole,
5-amino-2-phenyl-N-methyl-4-chloroimidazole,
5-amino-N-(2-hydroxyeth-1-yl)-4-chloroimidazole,
5-amino-2-methyl-N-(2-hydroxyeth-1-yl)-4-chloroimidazole,
5-amino-2-phenyl-N-(2-hydroxyeth-1-yl)-4-chloroimidazole,
5-amino-N-(phenyl)-4-chloroimidazole,
5-amino-2-methyl-N-(phenyl)-4-chloroimidazole,
5-amino-2-phenyl-N-(phenyl)-4-chloroimidazole,
5-methylamino-4-chloroimidazole,
5-methylamino-2-methyl-4-chloroimidazole,
5-methylamino-2-phenyl-4-chloroimidazole,
5-methylamino-N-methyl-4-chloroimidazole,
5-methylamino-2-methyl-N-methyl-4-chloroimidazole,
5-methylamino-2-phenyl-N-methyl-4-chloroimidazole,
5-methylamino-N-(2-hydroxyeth-1-yl)-4-chloroimidazole,
5-methylamino-2-methyl-N-(2-hydroxyeth-1-yl)-4-chloroimidazole,
5-methylamino-2-phenyl-N-(2-hydroxyeth-1-yl)-4-chloroimidazole,
5-methylamino-N-(phenyl)-4-chloroimidazole,
5-methylamino-2-methyl-N-(phenyl)-4-chloroimidazole,
5-methylamino-2-phenyl-N-(phenyl)-4-chloroimidazole,
5-dimethylamino-4-chloroimidazole,
5-dimethylamino-2-methyl-4-chloroimidazole,
5-dimethylamino-2-phenyl-4-chloroimidazole,
5-dimethylamino-N-methyl-4-chloroimidazole,
5-dimethylamino-2-methyl-N-methyl-4-chloroimidazole,
5-dimethylamino-2-phenyl-N-methyl-4-chloroimidazole,
5-dimethylamino-N-(2-hydroxyeth-1-yl)-4-chloroimidazole,
5-dimethylamino-2-methyl-N-(2-hydroxyeth-1-yl)-4-chloroimidazole,
5-dimethylamino-2-phenyl-N-(2-hydroxyeth-1-yl)-4-chloroimidazole,
5-dimethylamino-N-(phenyl)-4-chloroimidazole,
5-dimethylamino-2-methyl-N-(phenyl)-4-chloroimidazole,
5-dimethylamino-2-phenyl-N-(phenyl)-4-chloroimidazole,
5-(pyrrolidin-1-yl)-4-chloroimidazole,
5-(pyrrolidin-1-yl)-2-methyl-4-chloroimidazole,
5-(pyrrolidin-1-yl)-2-phenyl-4-chloroimidazole,
5-(pyrrolidin-1-yl)-N-methyl-4-chloroimidazole,
5-(pyrrolidin-1-yl)-2-methyl-N-methyl-4-chloroimidazole,
5-(pyrrolidin-1-yl)-2-phenyl-N-methyl-4-chloroimidazole,
5-(pyrrolidin-1-yl)-N-(2-hydroxyeth-1-yl)-4-chloroimidazole,
5-(pyrrolidin-1-yl)-2-methyl-N-(2-hydroxyeth-1-yl)-4-chloroimidazole,
5-(pyrrolidin-1-yl)-2-phenyl-N-(2-hydroxyeth-1-yl)-4-chloroimidazole,
5-(pyrrolidin-1-yl)-N-(phenyl)-4-chloroimidazole,
5-(pyrrolidin-1-yl)-2-phenyl-N-(phenyl)-4-chloroimidazole,
5-(3-hydroxypyrrolidin-1-yl)-4-chloroimidazole,
5-(3-hydroxypyrrolidin-1-yl)-2-methyl-4-chloroimidazole,
5-(3-hydroxypyrrolidin-1-yl)-2-phenyl-4-chloroimidazole,
5-(3-hydroxypyrrolidin-1-yl)-N-methyl-4-chloroimidazole,
5-(3-hydroxypyrrolidin-1-yl)-2-methyl-N-methyl-4-chloroimidazole,
5-(3-hydroxypyrrolidin-1-yl)-2-phenyl-N-methyl-4-chloroimidazole,
5-(3-hydroxypyrrolidin-1-yl)-N-(2-hydroxyeth-1-yl)-4-chloroimidazole,
5-(3-hydroxypyrrolidin-1-yl)-2-methyl-N-(2-hydroxyeth-1-yl)-4-chloroimidazole,
5-(3-hydroxypyrrolidin-1-yl)-2-phenyl-N-(2-hydroxyeth-1-yl)-4-chloroimidazole,
5-(3-hydroxypyrrolidin-1-yl)-N-(phenyl)-4-chloroimidazole,
5-(3-hydroxypyrrolidin-1-yl)-2-methyl-N-(phenyl)-4-chloroimidazole,
5-(3-hydroxypyrrolidin-1-yl)-2-phenyl-N-(phenyl)-4-chloroimidazole,
5-(piperidin-1-yl)-4-chloroimidazole,
5-(piperidin-1-yl)-2-methyl-4-chloroimidazole,
5-(piperidin-1-yl)-2-phenyl-4-chloroimidazole,
5-(piperidin-1-yl)-N-methyl-4-chloroimidazole,
5-(piperidin-1-yl)-2-methyl-N-methyl-4-chloroimidazole,
5-(piperidin-1-yl)-2-phenyl-N-methyl-4-chloroimidazole,
5-(piperidin-1-yl)-N-(2-hydroxyeth-1-yl)-4-chloroimidazole,
5-(piperidin-1-yl)-2-methyl-N-(2-hydroxyeth-1-yl)-4-chloroimidazole,
5-(piperidin-1-yl)-2-phenyl-N-(2-hydroxyeth-1-yl)-4-chloroimidazole,
5-(piperidin-1-yl)-N-(phenyl)-4-chloroimidazole,
5-(piperidin-1-yl)-2-methyl-N-(phenyl)-4-chloroimidazole,
5-(piperidin-1-yl)-2-phenyl-N-(phenyl)-4-chloroimidazole,
5-(2-hydroxyethyl)amino-4-chloroimidazole,
5-(2-hydroxyethyl)amino-2-methyl-4-chloroimidazole,
5-(2-hydroxyethyl)amino-2-phenyl-4-chloroimidazole,
5-(2-hydroxyethyl)amino-N-methyl-4-chloroimidazole,
5-(2-hydroxyethyl)amino-2-methyl-N-methyl-4-chloroimidazole,
5-(2-hydroxyethyl)amino-2-phenyl-N-methyl-4-chloroimidazole,
5-(2-hydroxyethyl)amino-N-(2-hydroxyeth-1-yl)-4-chloroimidazole,
5-(2-hydroxyethyl)amino-2-methyl-N-(2-hydroxyeth-1-yl)-4-chloroimidazole,
5-(2-hydroxyethyl)amino-2-phenyl-N-(2-hydroxyeth-1-yl)-4-chloroimidazole,
5-(2-hydroxyethyl)amino-N-(phenyl)-4-chloroimidazole,
5-(2-hydroxyethyl)amino-2-methyl-N-(phenyl)-4-chloroimidazole, 5-(2-hydroxyethyl)amino-2-phenyl-N-(phenyl)-4-chloroimidazole, and the addition salts thereof with an acid or a base.

Among the compounds of formula (I), non-limiting mention may also be made of the following, for example:

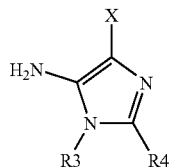

wherein the radicals X, R3 and R4 are as defined above. Among these compounds, for instance, in one embodiment, X may be chosen from a hydrogen atom and alkyl radicals, R3 may be chosen from a hydrogen atom, and alkyl radicals optionally substituted with a hydroxyl, and R4 may be chosen from a hydrogen atom and alkyl radicals.

By way of non-limiting example, the compounds of formula (I) may be, for example, chosen from:
5-amino-2-methylimidazole;
5-amino-2-methyl-(2,3-dihydroxypropyl)imidazole;
5-amino-1,2-dimethylimidazole;
5-amino-1-(2-hydroxy)ethyl-2-methylimidazole;
2-(5-amino-2-methylimidazol-1-yl)ethyl ester of benzoic acid;
2-(5-amino-2-methylimidazol-4-ylsulphanyl)acetamide and the addition salts thereof with an acid or a base.

The compounds of the present disclosure may be obtained for example from imidazole reagents substituted with a nitro radical, which are reduced by conventional reducing methods.

The composition according to the present disclosure can be used for the oxidation dyeing of keratinous fibers, such as human keratinous fibers.

The oxidation dyeing composition of the present disclosure comprises at least one oxidation base conventionally used in oxidation dyeing. By way of non-limiting example, these oxidation bases can be chosen from, for example, para-phenylenediamines, bisphenylalkylenediamines, para-aminophenols, ortho-aminophenols, heterocyclic bases, and the addition salts thereof with an acid or a base.

Among the para-phenylenediamines that may be used, non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and the addition salts thereof with an acid or a base.

Among the para-phenylenediamines mentioned above, non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof with an acid or a base.

Among the bisphenylalkylenediamines that may be used, non-limiting mention may be made, for example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylene-diamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof with an acid or a base.

Among the para-aminophenols that may be used, non-limiting mention may be made, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethyl phenol, 4-amino-2-(β-hydroxyethylaminomethyl)phenol, 4-amino-2-fluorophenol, and the addition salts thereof with an acid or a base.

Among the ortho-aminophenols that may be used, non-limiting mention may be made of, for example, 2-aminophenol, 2-amino-5-methylphenol, 2-amino-6-methylphenol, 5-acetamido-2-aminophenol, and the addition salts thereof with an acid or a base.

Among the heterocyclic bases that may be used, non-limiting mention may be made, by way of example, of pyridine derivatives, pyrimidine derivatives and pyrazole derivatives.

Among the pyridine derivatives that may be used, non-limiting mention may be made of the compounds described, for example, in the British Patent Nos. GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the addition salts thereof with an acid or a base.

Among the pyrimidine derivatives that may be used, non-limiting mention may be made of the compounds described, for example, in the following patents: DE 2,359,399; JP 88-169,571; JP 05,163,124; EP 0,770,375 and Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in the Patent Application FR-A-2,750,048, and among which, non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7- dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, the acid addition salts thereof, and their tautomeric forms, when a tautomeric equilibrium exists.

Among the pyrazole derivatives that may be used, non-limiting mention may be made of the compounds described in the following Patent Nos: DE 3,843,892, DE 4,133,957 and Patent Applications WO 94/08969, WO 94/08970, FR-A-2,733,749 and DE 195 43 988, which describe, for instance, 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-d iamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof with an acid or a base.

The at least one oxidation base may each be present in an amount ranging from 0.001 to 10% by weight, relative to the total weight of the dyeing composition, such as ranging from 0.005 to 6%.

The composition according to the present disclosure may further comprise at least one additional coupler conventionally used for dyeing keratinous fibers. Among these additional couplers, non-limitng mention may be made, for example, of meta-phenylenediamines, meta-aminophenols, meta-diphenols, naphthalene couplers, heterocyclic couplers other than those of the imidazole type according to the present disclosure, and the addition salts thereof with an acid or a base.

By way of non-limiting example, there may be mentioned 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene and the addition salts thereof with an acid or a base.

In the composition according to the present disclosure, the at least one coupler may each generally be present in an amount ranging from 0.001 to 10% by weight, relative to the total weight of the dyeing composition, such as, ranging from 0.005 to 6% by weight.

In general, the addition salts of the oxidation bases and of the couplers that can be used in the context of the present disclosure may be chosen from, for example, acid addition salts, such as hydrochlorides, hydrobromides, sulphates, citrates, succinates, tartrates, lactates, tosylates, benzenesulphonates, phosphates and acetates and basic addition salts, such as sodium hydroxide, potassium hydroxide, ammonium hydroxide, amines and alkanolamines.

The dyeing composition in accordance with the present disclosure may additionally comprise at least one direct dye that may be chosen, for example, from nitro dyes of the benzene series, azo direct dyes and methine direct dyes. The at least one direct dye may be chosen from nonionic, anionic and cationic direct dyes.

An appropriate dyeing medium, also called dye carrier, generally comprises water or a mixture of water and at least one organic solvent for solubilizing the compounds that would not be sufficiently soluble in water. By way of organic solvent, there may be mentioned, as non-limiting examples, $C_1$–$C_4$ lower alkanols such as ethanol and isopropanol; polyols and polyol ethers such as 2-butoxyethanol, propylene glycol, propylene glycol monomethyl ether, diethylene glycol monoethyl ether and monomethyl ether; aromatic alcohols such as benzyl alcohol or phenoxyethanol, and mixtures thereof.

The solvents may be present in the composition, for example, in an amount ranging from 1 to 40% by weight, relative to the total weight of the dyeing composition, for instance from 5 to 30% by weight.

The dyeing composition in accordance with the present disclosure may also comprise various adjuvants that are conventionally used in hair dyeing compositions, such as anionic, cationic, nonionic, amphoteric and zwitterionic surfactants and mixtures thereof; anionic, cationic, nonionic, amphoteric and zwitterionic polymers and mixtures thereof; inorganic and organic thickeners; for instance anionic, cationic, nonionic and amphoteric polymeric associative thickeners, antioxidants, penetrating agents, sequestering agents, perfumes, buffers, dispersing agents, conditioning agents such as, for example, modified and unmodified, volatile and nonvolatile silicones, film-forming agents, ceramides, preservatives, and opacifying agents.

The above adjuvants may each be present in an amount ranging from 0.01 to 20% by weight, relative to the total weight of the composition.

Persons skilled in the art will be careful to choose any optional additional compounds such that the advantageous properties which are intrinsically attached to the oxidation dyeing composition in accordance with the present disclosure are not, or not substantially, impaired by any of the additions envisaged.

The pH of the dyeing composition in accordance with the present disclosure may range from 3 to 12, such as from 5 to 11. The pH may be adjusted to the desired value by means of acidifying or alkalinizing agents customarily used in dyeing keratinous fibers, or alternatively with the aid of conventional buffer systems.

Among the acidifying agents, there may be mentioned, by way of non-limiting example, inorganic and organic acids such as hydrochloric acid, orthophosphoric acid, sulphuric acid, carboxylic acids such as acetic acid, tartaric acid, citric acid, lactic acid, and sulphonic acids.

Among the alkalinizing agents, there may be mentioned, by way of non-limiting example, aqueous ammonia, alkali metal carbonates, alkanolamines such as mono-, di- and triethanolamines and their derivatives, sodium and potassium hydroxides and the compounds of formula (II):

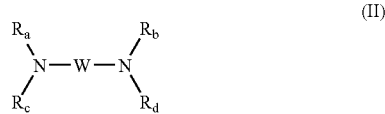

wherein W is a propylene residue that is optionally substituted with a radical chosen from hydroxyl groups and $C_1$–$C_4$ alkyl radicals; $R_a$, $R_b$, $R_c$ and $R_d$, which may be identical or different, can be chosen from hydrogen atoms, $C_1$–$C_4$ alkyl radicals and $C_1$–$C_4$ hydroxyalkyl radicals.

The dyeing composition according to the present disclosure may be provided in various forms, such as in the form of liquids, creams, gels, or in any other form appropriate for dyeing keratinous fibers, such as human hair.

Also disclosed herein is a process for dyeing keratinous fibers wherein the composition according to the present disclosure as defined above is applied to the fibers in the presence of an oxidizing agent for a time that is sufficient to obtain the desired coloration. The color may be developed at acidic, neutral or alkaline pH, and the oxidizing agent may be added to the composition as disclosed herein at the time of use, or the oxidizing agent may be used in the form of an oxidizing composition comprising at least one oxidizing agent, which may be applied simultaneously with or sequentially to the composition of the invention.

According to one embodiment, the composition according to the present disclosure is mixed, for instance at the time of use, with a composition comprising, in an appropriate dyeing medium, at least one oxidizing agent, wherein the at least one oxidizing agent is present in a sufficient amount to develop a coloration. The mixture obtained is then applied to keratinous fibers. After a leave-in time ranging from 3 to 50 minutes, such as from 5 to 30 minutes, the keratinous fibers are rinsed, washed with shampoo, rinsed again and then dried.

The oxidizing agents that may be used include those conventionally used for the oxidation dyeing of keratinous fibers, for example, hydrogen peroxide, urea peroxide, alkali metal bromates, persalts such as perborates and persulfates, peracids and oxidase enzymes among which there may be mentioned peroxidases, oxidoreductases containing two electrons such as uricases, and oxygenases containing four electrons such as laccases. For example, in one embodiment of the present disclosure, the at least one oxidizing agent is hydrogen peroxide.

The oxidizing composition may also comprise various adjuvants conventionally used in hair-dyeing compositions and as defined above.

The pH of the oxidizing composition comprising the at least one oxidizing agent is such that after mixing the oxidizing composition with the dyeing composition, the pH of the resulting composition applied to the keratinous fibers may range from 3 to 12, such as from 5 to 11. The pH may be adjusted to the desired value by means of acidifying or alkalinizing agents customarily used in dyeing keratinous fibers and as defined above.

This "ready-to-use" composition that is applied to the keratinous fibers may be provided in various forms, such as in the form of liquids, creams, gels or in any other form appropriate for dyeing keratinous fibers, such as human hair.

Another aspect of the present disclosure is a multicompartment device or dyeing "kit" wherein at least one first compartment comprises the dyeing composition of the present disclosure as defined above and at least one second compartment comprises at least one oxidizing agent. This device may be equipped with a means that enables the delivery of the desired mixture to the hair, such as the devices described in the patent FR-2-586,913.

Using this device or kit, it is possible to dye keratinous fibers using a process that comprises mixing a dyeing composition comprising at least one oxidation base of formula (I) with at least one oxidizing agent, and applying the mixture obtained to keratinous fibers for a sufficient time to develop the desired coloration.

The compounds of formula (I) may be obtained according to methods of synthesis known in the field of synthesis of heterocycles.

By way of non-limiting example, the imidazole derivatives alkylated at the 1-position are obtained by the method described in *Heterocyclic Chemistry, A. R. Katritsky, Chapter: Single Ring With Two Heteroatom*, by reacting the nitroimidazoles 1 with the reagent $R_3X_1$ wherein $R_3$ is an alkyl radical according to the above definition and $X_1$ is a nucleofuge, such as a halide, an O-sulphonate in an apolar or polar solvent, and in the presence of a base such as an alcoholate, or a metal hydride at a temperature ranging from −20° C. to 60° C. When $R_3$ is a phenyl radical according to the above definition and $X_1$ is a halide, then a catalyst based on palladium (0) or palladium (II) is added to the reaction medium in order to carry out the nitrogen carbon N—C coupling according to the Hartwig-Buchwald procedure (Hartwig, J. F. *Synlett* 1997, 329; *Acc. Chem. Res.* 1998, 31, 805; *J. Org. Chem.* 1996, 61, 7240). After brominating by the action of bromine or N-bromosuccinimide, or chlorinating by the action of N-chlorosuccinimide at the 5-position, the derivatives 3 are obtained. The addition-elimination at the 5-position of the imidazole derivative 3 with a nucleophile of formula X⁻ such as a phenate or an alcoholate, or alternatively a thiolate optionally substituted as defined above leads to the nitro compounds 4. These are then subjected to a hydrogenation reaction by heterogeneous catalysis such as Pd/C, Pd(II)/C, Ni/Ra, and the like, or alternatively to a reduction reaction with a metal such as zinc, iron, tin, and the like (see *Advanced Organic Chemistry*, 3$^{rd}$ edition, J. March, and Reduction in organic Chemistry, M. Hudlicky). The functionalization of the primary amine at the 4 position to the secondary and tertiary amines $NR_1R_2$ (optionally forming a ring) is carried out according to conventional methods of organic synthesis (alkyl halide, alkyl O-sulphonate, alkyl trialkylammonium, reductive amination, and the like, see, for example *Advanced Organic Chemistry*, 3$^{rd}$ edition, J. March).

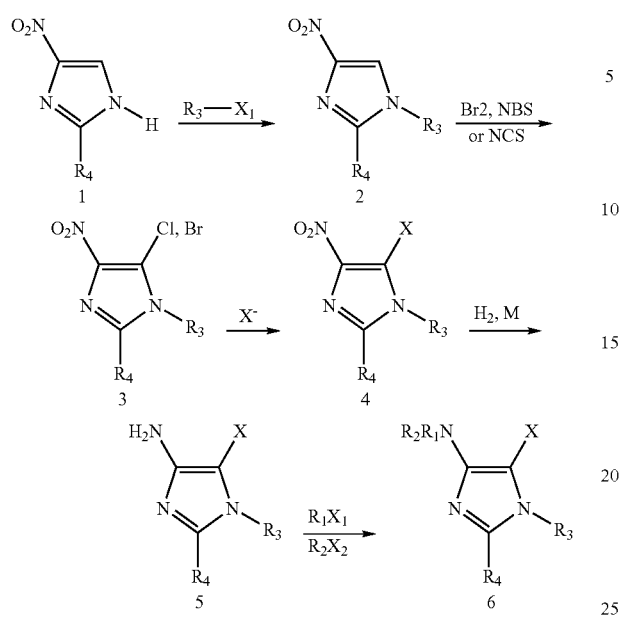

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The examples which follow serve to illustrate the invention without however being of a limiting nature.

EXAMPLES

General Procedure Used:

To an aqueous-alcoholic solution comprising a protic acid such as hydrochloric acid, ammonium chloride, acetic acid or sulphuric acid, and 0.5 g of zinc in powdered form, was added the nitroimidazole derivative at a temperature ranging from 20° C. to 80° C. After complete consumption of the nitro starting material, the reaction mixture was concentrated until a solid precipitated, after which the solid was filtered, washed with diisopropyl ether and dried to constant weight.

Example 1

The compound below (5-amino-2-methylimidazole) was obtained by reducing under the conditions described above the compound 5-nitro-2-methylimidazole:

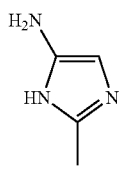

Example 2

The compound below (5-amino-2-methyl-(2,3-dihydroxypropyl)imidazole) was obtained by reducing under the conditions described above the compound 5-nitro-2-methyl-(2,3-dihydroxypropyl)imidazole:

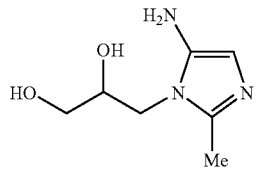

Example 3

The compound below (5-amino-1,2-dimethylimidazole) was obtained by reducing under the conditions described above the compound 5-nitro-1,2-dimethylimidazole:

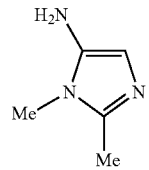

Example 4

The compound below (5-amino-1-(2-hydroxy)ethyl-2-methylimidazole) was obtained by reducing under the conditions described above the compound 5-nitro-1-(2-hydroxy)ethyl-2-methylimidazole:

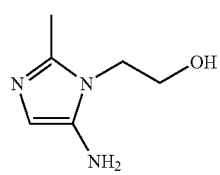

Example 5

The compound below (2-(5-amino-2-methylimidazol-1-yl)ethyl ester of benzoic acid) was obtained by reducing under the conditions described above the compound 2-(5-nitro-2-methylimidazol-1-yl)ethyl ester of benzoic acid:

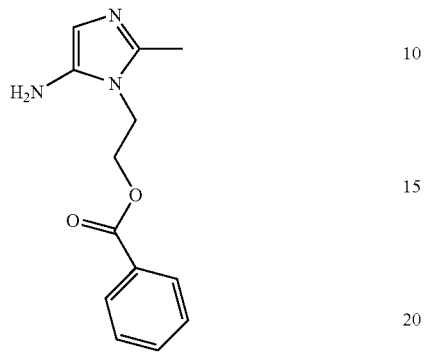

Example 6

The compound below (2-(5-amino-2-methylimidazol-4-ylsulphanyl)acetamide) was obtained by reducing under the conditions described above the compound 2-(5-nitro-2-methylimidazol-4-ylsulphanyl)acetamide:

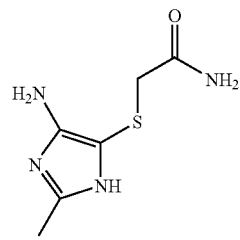

Examples of Dyeing

|  | Examples | | | | | |
| --- | --- | --- | --- | --- | --- | --- |
|  | 1 | 2 | 3 | 4 | 5 | 6 |
| 5-amino-2-methylimidazole | $4 \times 10^{-4}$ mole | | | | | |
| 5-amino-2-methyl-(2,3-dihydroxypropyl)imidazole | | $4 \times 10^{-4}$ mole | | | | |
| 5-amino-1,2-dimethylimidazole | | | $4 \times 10^{-4}$ mole | | | |
| 5-amino-1-(2-hydroxy)-ethyl-2-methylimidazole | | | | $4 \times 10^{-4}$ mole | | |
| 2-(5-amino-2-methyl-imidazol-1-yl)ethyl ester of benzoic acid | | | | | $4 \times 10^{-4}$ mole | |
| 2-(5-amino-2-methyl-imidazol-4-ylsulphanyl)-acetamide | | | | | | $4 \times 10^{-4}$ mole |
| 3,7-diamino-5-methyl-pyrazolo[1,5-a]pyrimidine | $4 \times 10^{-4}$ mole | $4 \times 10^{-4}$ mole | $4 \times 10^{-4}$ mole | $4 \times 10^{-4}$ mole | $4 \times 10^{-4}$ mole | $4 \times 10^{-4}$ Mole |
| Dye carrier (1) | (*) | (*) | (*) | (*) | (*) | (*) |
| Demineralized water qs | 100 g | 100 g | 100 g | 100 g | 100 g | 100 g |

(*) Dye carrier pH 7

| | |
| --- | --- |
| DMSO | 0.18 g |
| Ethyl alcohol, 96% | 9.3 g |
| Methyl alcohol | 39.7 g |
| Acetic acid | 4.4 g |
| Sodium metabisulphite | 0.204 g |
| Pentasodium salt of diethylene-triaminopentaacetic acid in aqueous solution at 40% | 1.1 g |
| $C_8$–$C_{15}$ alkyl polyglucoside sold in solution at 60% under the name ORAMIXCG110 by the company SEPPIC | 5.3 g |
| Benzyl alcohol | 1.8 g |
| Polyethylene glycol containing 8 mol of EO | 2.7 g |
| Ammonium chloride buffer 0.5M pH 7 | 31.0 g |

At the time of use, each dye composition was mixed with an equal weight of hydrogen peroxide at 20 volumes (6% by weight). A final pH of 7 was obtained.

Each mixture obtained was applied to locks of grey hair that were 90% white. After leaving in for 30 min, the locks were rinsed, washed with a standard shampoo, rinsed again and then dried.

The following dyeing results were obtained.

| | Example | | | | | |
|---|---|---|---|---|---|---|
| | 1 | 2 | 3 | 4 | 5 | 6 |
| Shade observed | pink-brown | orange-pink | orange-pink | orange-pink | orange-pink | pink-brown |

What is claimed is:

1. A compound of the imidazole type of formula (I) and the addition salts thereof with an acid or a base:

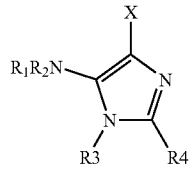

(I)

wherein:
$R_1$, $R_2$ and $R_4$, which may be identical or different, are chosen from
 hydrogen atoms;
 phenyl radicals optionally substituted with at least one entity chosen from halogens and hydroxyl, $C_1-C_4$ alkoxy, carboxyl, carboxamido, $(C_1-C_4)$alkylsulphonyl, sulphonic, alkylsulphoxide, alkylsulphonamido, $NR_{13}R_{14}$, and $C_1-C_4$ alkyl radicals, wherein the $C_1-C_4$ alkyl radicals are optionally substituted with at least one radical chosen from hydroxyl, $C_1-C_4$ alkoxy, carboxyl, carboxamido, $(C_1-C_4)$alkylsulphonyl, sulphonic, alkylsulphoxide, alkylsulphonamido and $NR_{13}R_{14}$ radicals;
 linear and branched $C_1-C_8$ alkyl radicals optionally substituted with at least one radical chosen from hydroxyl, $C_1-C_2$ alkoxy, carboxyl, carboxamido, $(C_1-C_4)$alkylsulphonyl, sulphonic, alkylsulphoxide, alkylsulphonamido and $NR_{13}R_{14}$ radicals,
$R_4$ may also be chosen from:
 $NR_{22}R_{23}$ radicals wherein $R_{22}$ and $R_{23}$, which may be identical or different, are chosen from hydrogen atoms, acyl radicals, $C_1-C_2$ alkyl radicals optionally substituted with a radical chosen from hydroxyl and $C_1-C_2$ alkoxy radicals,
 5- and 6-membered aromatic heterocycles optionally substituted with at least one entity chosen from hydroxyl, $C_1-C_2$ alkoxy, amino, dimethylamino, 2-hydroxyethylamino, bis(2-hydroxyethyl)amino radicals and chlorine atoms,
$R_1$ and $R_2$ may form with the nitrogen atom to which they are attached a 5- to 8-membered heterocycle in which at least one carbon atom of the carbon ring may be replaced by an entity chosen from oxygen, nitrogen and sulphur atoms and $SO_2$ groups; the carbon atoms of the ring may be substituted with a radical $R_5$; and with the proviso that the ring does not comprise a peroxide bond, or diazo or nitroso radicals;
$R_5$ is chosen from:
 halogen atoms;
 $C_1-C_4$ alkyl radicals optionally substituted with at least one radical chosen from hydroxyl, carboxyl, $C_1-C_4$ alkoxycarbonyl, $C_1-C_4$ alkoxy and $NR_6R_7$ radicals;
 carboxyl radicals;
 carboxamido radicals;
 $(C_1-C_4)$alkylsulphonyl radicals;
 alkylsulphonamido radicals;
 hydroxyl radicals;
 $C_1-C_4$ alkoxy radicals;
 $C_2-C_4$ hydroxyalkoxy radicals;
 aminosulphonyl radicals;
 $C_1-C_4$ thioether radicals;
 $(C_1-C_4)$alkylsulphoxide radicals;
 $(C_1-C_4)$alkylsulphonyl radicals;
 a radical $NR_8R_9$;
$R_3$ is chosen from
 $(C_1-C_4)$alkylsulphonyl radicals;
 linear and branched $C_1-C_8$ alkyl radicals substituted with at least one radical chosen from hydroxyl, $OR_{10}$, carboxyl, carboxamido, $(C_1-C_4)$alkylsulphonyl, sulphonic, $(C_1-C_4)$alkylsulphoxide, alkylsulphonamido and $NR_{11}R_{12}$ radicals;
 phenyl radicals and 5- and 6-membered aromatic heterocycles, wherein these radicals are optionally substituted with at least one entity chosen from halogens, hydroxyl, $C_1-C_4$ alkoxy, carboxyl, carboxamido, $(C_1-C_4)$alkylsulphonyl, sulphonic, alkylsulphoxide, $C_1-C_4$ thioether, alkylsulphonamido, $NR_{13}R_{14}$, and $C_1-C_4$ alkyl radicals, wherein the $C_1-C_4$ alkyl radicals are optionally substituted with at least one radical chosen from hydroxyl, $C_1-C_4$ alkoxy, carboxyl, carboxamido, $(C_1-C_4)$ alkylsulphonyl, sulphonic, alkylsulphoxide, alkylsulphonamido and $NR_{13}R_{14}$ radicals;
$R_{10}$ is chosen from $C_1-C_4$ alkyl radicals optionally substituted with at least one radical chosen from hydroxyl, $C_1-C_2$ alkoxy, amino, (di)$(C_1-C_4)$alkylamino and $C_2-C_4$ (poly)hydroxyalkylamino radicals,
$R_6$, $R_7$, $R_8$, $R_9$, $R_{11}$, $R_{12}$, $R_{13}$, $R_{14}$, which may be identical or different, are chosen from hydrogen atoms, acyl radicals, carboxamido radicals, $C_1-C_4$ alkyl radicals optionally substituted with at least one radical chosen from hydroxyl, $C_1-C_4$ alkoxy, sulphino, $(C_1-C_4)$alkylsulphonyl, alkylsulphonamido, carboxyl, carboxamido, alkylsulphoxide, amino, mono- and di$(C_1-C_4)$alkylamino, and $C_2-C_4$ (poly)hydroxyalkylamino radicals;
$R_{11}$ and $R_{12}$ may also form with the nitrogen atom carrying them a 5- to 8-membered ring optionally substituted with at least one entity chosen from halogen atoms, hydroxyl, $C_1-C_4$ alkoxy, carboxyl, carbamyl, $(C_1-C_4)$alkylsulphonyl, sulphonic, alkylsulphoxide, $C_1-C_4$ thioether, alkylsulphonamido, $NR_{13}R_{14}$, and $C_1-C_4$ alkyl radicals, wherein the $C_1-C_4$ alkyl radicals are optionally substituted with at least one radical chosen from hydroxyl, $C_1-C_4$ alkoxy, carboxyl, carboxamido, $(C_1-C_4)$alkylsulphonyl, sulphonic, alkylsulphoxide, alkylsulphonamido and $NR_{13}R_{14}$ radicals,
X is chosen from hydrogen atoms; halogen atoms; $C_1-C_4$ alkoxy radicals; phenoxy radicals optionally substituted with at least one entity chosen from halogens, hydroxyl, $C_1-C_4$ alkoxy, carboxyl, $C_1-C_4$ alkoxycarbonyl, carboxamido, sulphino, $(C_1-C_4)$alkylsulphonyl, sulphonic, alkylsulphoxide, $C_1-C_4$ thioether, alkylsulphonamido, $NR_{13}R_{14}$, and $C_1$–$C_4$ alkyl radicals; $C_1$–$C_4$ thioether radicals optionally substituted with at least one radical chosen from hydroxyl, $C_1$–$C_2$ alkoxy, carboxyl, and sulphonic radicals.

2. The compound according to claim 1, wherein $R_1$ and $R_2$, which may be identical or different, are chosen from:
hydrogen atoms;
phenyl radicals optionally substituted with at least one radical chosen from hydroxyl, $C_1$–$C_4$ alkoxy, carboxamido, alkylsulphoxide, alkylsulphonamido, $N_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxamido, alkylsulphonamido and $NR_{13}R_{14}$ radicals, and
linear and branched $C_1$–$C_6$ alkyl radicals optionally substituted with at least one radical chosen from hydroxyl, $C_1$–$C_2$ alkoxy, carboxyl, carboxamido, $(C_1$–$C_4)$alkylsulphonyl, sulphonic, alkylsulphoxide, alkylsulphonamido and $NR_{13}R_{14}$ radicals.

3. The compound according to claim 2, wherein $R_1$ and $R_2$, which may be identical or different, are chosen from hydrogen atoms; phenyl radicals; linear and branched $C_1$–$C_4$ alkyl radicals substituted with at least one radical chosen from hydroxyl, $C_1$–$C_2$ alkoxy, amino, di$(C_1$–$C_4)$alkylamino, carboxyl, a carboxamido, alkylsulphonamido, and $NR_{13}R_{14}$ radicals, wherein $R_{13}$ and $R_{14}$ which may be identical or different, are chosen from hydrogen atoms, acyl radicals, $C_1$–$C_2$ alkyl radicals optionally substituted with an entity chosen from hydroxyl, and $C_1$–$C_2$ alkoxy radicals.

4. The compound according to claim 3, wherein $R_1$ and $R_2$, which may be identical or different, are chosen from hydrogen atoms, and methyl, 2-hydroxyethyl, 2-carboxyethyl and 1,2-dihydroxyethyl radicals.

5. The compound according to claim 1, wherein $R_1$ and $R_2$ form with the nitrogen atom to which they are attached a 5- to 8-membered heterocycle chosen from pyrrolidine, piperidine, homopiperidine, piperazine, and homopiperazine rings, it being possible for the rings to be substituted with at least one $R_5$ radical.

6. The compound according to claim 5, wherein $R_1$ and $R_2$ form together with the nitrogen atom to which they are attached a heterocycle chosen from 2,5-dimethylpyrrolidine, proline, 3-hydroxyproline, 4-hydroxyproline, 2,4-dicarboxy-pyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylamino-pyrrolidine, 4-amino-3-hydroxypyrrolidine, 3-hydroxy-4-(2-hydroxyethyl)aminopyrrolidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-β-hydroxyethylhomopiperazine and the addition salts thereof.

7. The compound according to claim 6, wherein $R_1$ and $R_2$ form together with the nitrogen atom to which they are attached a heterocycle chosen from pyrrolidine, 3-hydroxypyrrolidine, 3-aminopyrrolidine, proline, 3-hydroxyproline, piperidine, 3- and 4-hydroxypiperidine, homopiperidine, homopiperazine, N-methylhomopiperazine, N-β-hydroxyethylhomopiperazine and the addition salts thereof.

8. The compound according to claim 1, wherein $R_3$ is chosen from hydroxyalkyl radicals, alkylsulphonyl radicals and phenyl radicals.

9. The compound according to claim 1, wherein $R_4$ is chosen from hydrogen atoms; amino radicals; sulphonic radicals; sulphoxide radicals; sulphonylamino radicals; linear and branched $C_1$–$C_6$ alkyl radicals optionally substituted with at least one radical chosen from hydroxyl, $C_1$–$C_2$ alkoxy, amino, carboxyl, carboxamido, and alkylsulphonamido radicals; $NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals; phenyl radicals; and 5- and 6-membered aromatic heterocycles optionally substituted with at least one radical chosen from hydroxyl, $C_1$–$C_2$ alkoxy, amino, (di-)methylamino, 2-hydroxyethylamino, and bis(2-hydroxyethyl) amino radicals and chlorine atoms.

10. The compound according to claim 9, wherein $R_4$ is chosen from hydrogen atoms and alkyl radicals.

11. The compound according to claim 1, wherein X is chosen from hydrogen atoms, halogens, and alkoxy radicals.

12. The compound according to claim 1, chosen from:
5-amino-N-(2-hydroxyeth-1-yl)imidazole,
5-amino-2-methyl-N-(2-hydroxyeth-1-yl)imidazole,
5-amino-2-phenyl-N-(2-hydroxyeth-1-yl)imidazole,
5-amino-N-(phenyl)imidazole,
5-amino-2-methyl-N-(phenyl)imidazole,
5-amino-2-phenyl-N-(phenyl)imidazole,
5-methylamino-N-(2-hydroxyeth-1-yl)imidazole,
5-methylamino-2-methyl-N-(2-hydroxyeth-1-yl)imidazole,
5-methylamino-2-phenyl-N-(2-hydroxyeth-1-yl)imidazole,
5-methylamino-N-(phenyl)imidazole,
5-methylamino-2-methyl-N-(phenyl)imidazole,
5-methylamino-2-phenyl-N-(phenyl)imidazole,
5-dimethylamino-N-(2-hydroxyeth-1-yl)imidazole,
5-dimethylamino-2-methyl-N-(2-hydroxyeth-1-yl)imidazole,
5-dimethylamino-2-phenyl-N-(2-hydroxyeth-1-yl)imidazole,
5-dimethylamino-N-(phenyl)imidazole,
5-dimethylamino-2-methyl-N-(phenyl)imidazole,
5-dimethylamino-2-phenyl-N-(phenyl)imidazole,
5-(pyrrolidin-1-yl)-N-(2-hydroxyeth-1-yl)imidazole,
5-(pyrrolidin-1-yl)-2-methyl-N-(2-hydroxyeth-1-yl)imidazole,
5-(pyrrolidin-1-yl)-2-phenyl-N-(2-hydroxyeth-1-yl)imidazole,
5-(pyrrolidin-1-yl)-N-(phenyl)imidazole,
5-(pyrrolidin-1-yl)-2-methyl-N-(phenyl)imidazole,
5-(pyrrolidin-1-yl)-2-phenyl-N-(phenyl)imidazole,
5-(3-hydroxypyrrolidin-1-yl)-N-(2-hydroxyeth-1-yl)imidazole,
5-(3-hydroxypyrrolidin-1-yl)-2-methyl-N-(2-hydroxyeth-1-yl)imidazole,
5-(3-hydroxypyrrolidin-1-yl)-2-phenyl-N-(2-hydroxyeth-1-yl)imidazole,
5-(3-hydroxypyrrolidin-1-yl)-N-(phenyl)imidazole,
5-(3-hydroxypyrrolidin-1-yl)-2-methyl-N-(phenyl)imidazole,
5-(3-hydroxypyrrolidin-1-yl)-2-phenyl-N-(phenyl)imidazole,
5-(piperidin-1-yl)-N-(2-hydroxyeth-1-yl)imidazole,
5-(piperidin-1-yl)-2-methyl-N-(2-hydroxyeth-1-yl)imidazole, 5-(piperidin-1-yl)-2-phenyl-N-(2-hydroxyeth-1-yl)imidazole,
5-(piperidin-1-yl)-N-(phenyl)imidazole,
5-(piperidin-1-yl)-2-methyl-N-(phenyl)imidazole,
5-(piperidin-1-yl)-2-phenyl-N-(phenyl)imidazole,
5-(2-hydroxyethyl)amino-N-(2-hydroxyeth-1-yl)imidazole,
5-(2-hydroxyethyl)amino-2-methyl-N-(2-hydroxyeth-1-yl)imidazole,
5-(2-hydroxyethyl)amino-2-phenyl-N-(2-hydroxyeth-1-yl)imidazole,
5-(2-hydroxyethyl)amino-N-(phenyl)imidazole,
5-(2-hydroxyethyl)amino-2-methyl-N-(phenyl)imidazole,
5-(2-hydroxyethyl)amino-2-phenyl-N-(phenyl)imidazole,
5-amino-N-(2-hydroxyeth-1-yl)-4-chloroimidazole,
5-amino-2-methyl-N-(2-hydroxyeth-1-yl)-4-chloroimidazole,
5-amino-2-phenyl-N-(2-hydroxyeth-1-yl)-4-chloroimidazole,
5-amino-N-(phenyl)-4-chloroimidazole,
5-amino-2-methyl-N-(phenyl)-4-chloroimidazole,
5-amino-2-phenyl-N-(phenyl)-4-chloroimidazole,
5-methylamino-N-(2-hydroxyeth-1-yl)-4-chloroimidazole,
5-methylamino-2-methyl-N-(2-hydroxyeth-1-yl)-4-chloroimidazole,
5-methylamino-2-phenyl-N-(2-hydroxyeth-1-yl)-4-chloroimidazole,
5-methylamino-N-(phenyl)-4-chloroimidazole,
5-methylamino-2-methyl-N-(phenyl)-4-chloroimidazole,
5-methylamino-2-phenyl-N-(phenyl)-4-chloroimidazole,
5-dimethylamino-N-(2-hydroxyeth-1-yl)-4-chloroimidazole,
5-dimethylamino-2-methyl-N-(2-hydroxyeth-1-yl)-4-chloroimidazole,
5-dimethylamino-2-phenyl-N-(2-hydroxyeth-1-yl)-4-chloroimidazole,
5-dimethylamino-N-(phenyl)-4-chloroimidazole,
5-dimethylamino-2-methyl-N-(phenyl)-4-chloroimidazole,
5-dimethylamino-2-phenyl-N-(phenyl)-4-chloroimidazole,
5-(pyrrolidin-1-yl)-N-(2-hydroxyeth-1-yl)-4-chloroimidazole,
5-(pyrrolidin-1-yl)-2-methyl-N-(2-hydroxyeth-1-yl)-4-chloroimidazole,
5-(pyrrolidin-1-yl)-2-phenyl-N-(2-hydroxyeth-1-yl)-4-chloroimidazole,
5-(pyrrolidin-1-yl)-N-(phenyl)-4-chloroimidazole,
5-(pyrrolidin-1-yl)-2-methyl-N-(phenyl)-4-chloroimidazole,
5-(pyrrolidin-1-yl)-2-phenyl-N-(phenyl)-4-chloroimidazole,
5-(3-hydroxypyrrolidin-1-yl)-N-(2-hydroxyeth-1-yl)-4-chloroimidazole,
5-(3-hydroxypyrrolidin-1-yl)-2-methyl-N-(2-hydroxyeth-1-yl)-4-chloroimidazole,
5-(3-hydroxypyrrolidin-1-yl)-2-phenyl-N-(2-hydroxyeth-1-yl)-4-chloroimidazole,
5-(3-hydroxypyrrolidin-1-yl)-N-(phenyl)-4-chloroimidazole,
5-(3-hydroxypyrrolidin-1-yl)-2-methyl-N-(phenyl)-4-chloroimidazole,
5-(3-hydroxypyrrolidin-1-yl)-2-phenyl-N-(phenyl)-4-chloroimidazole,
5-(piperidin-1-yl)-N-(2-hydroxyeth-1-yl)-4-chloroimidazole,
5-(piperidin-1-yl)-2-methyl-N-(2-hydroxyeth-1-yl)-4-chloroimidazole,
5-(piperidin-1-yl)-2-phenyl-N-(2-hydroxyeth-1-yl)-4-chloroimidazole,
5-(piperidin-1-yl)-N-(phenyl)-4-chloroimidazole,
5-(piperidin-1-yl)-2-methyl-N-(phenyl)-4-chloroimidazole,
5-(piperidin-1-yl)-2-phenyl-N-(phenyl)-4-chloroimidazole,
5-(2-hydroxyethyl)amino-N-(2-hydroxyeth-1-yl)-4-chloroimidazole,
5-(2-hydroxyethyl)amino-2-methyl-N-(2-hydroxyeth-1-yl)-4-chloroimidazole,
5-(2-hydroxyethyl)amino-2-phenyl-N-(2-hydroxyeth-1-yl)-4-chloroimidazole,
5-(2-hydroxyethyl)amino-N-(phenyl)-4-chloroimidazole,
5-(2-hydroxyethyl)amino-2-methyl-N-(phenyl)-4-chloroimidazole,
5-(2-hydroxyethyl)amino-2-phenyl-N-(phenyl)-4-chloroimidazole,
and the addition salts thereof with an acid or a base.

13. The compound according to claim 1, chosen from:
5-amino-2-methyl-(2,3-dihydroxypropyl)imidazole;
5-amino-1-(2-hydroxy)ethyl-2-methylimidazole;
2-(5-amino-2-methylimidazol-1-yl)ethyl ester of benzoic acid;
2-(5-amino-2-methylimidazol-4-ylsulphanyl)acetamide
and the addition salts thereof with an acid or a base.

14. The compound according to claim 1, wherein the formula is

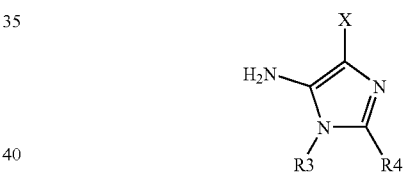

wherein, X, R3 and R4 are as defined in claim 1.

15. The compound according to claim 14, wherein X is chosen from hydrogen atoms and alkyl radicals, R3 is chosen from alkyl radicals substituted with a hydroxyl and R4 is chosen from hydrogen atoms and alkyl radicals.

16. An nitro intermediate compound of formula:

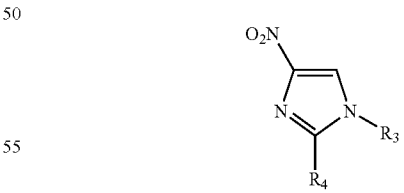

wherein
$R_4$ is chosen from
a hydrogen atom;
phenyl radicals optionally substituted with at least one entity chosen from halogens and hydroxyl, $C_1$–$C_4$ alkoxy, carboxyl, carboxamido, ($C_1$–$C_4$)alkylsulphonyl, sulphonic, alkylsulphoxide, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals;

linear and branched $C_1$–$C_8$ alkyl radicals optionally substituted with at least one radical chosen from hydroxyl, $C_1$–$C_2$ alkoxy, carboxyl, carboxamido, $(C_1$–$C_4)$alkylsulphonyl, sulphonic, alkylsulphoxide, alkylsulphonamido and $NR_{13}R_{14}$ radicals, $NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals, 5- and 6-membered aromatic heterocycles optionally substituted with at least one entity chosen from hydroxyl, $C_1$–$C_2$ alkoxy, amino, dimethylamino, 2-hydroxyethylamino, bis(2-hydroxyethyl)amino radicals and chlorine atoms, $R_3$ is chosen from
$(C_1$–$C_4)$alkylsulphonyl radicals;

phenyl radicals and 5- and 6-membered aromatic heterocycles, wherein these radicals are optionally substituted with at least one entity chosen from halogens, hydroxyl, $C_1$–$C_4$ alkoxy, carboxyl, carboxamido, $(C_1$–$C_4)$alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals;

$R_{10}$ is chosen from $C_1$–$C_4$ alkyl radicals optionally substituted with at least one radical chosen from hydroxyl, $C_1$–$C_2$ alkoxy, amino, $(di)(C_1$–$C_4)$alkylamino and $C_2$–$C_4$ (poly)hydroxyalkylamino radicals, $R_{11}$, $R_{12}$, $R_{13}$, $R_{14}$, which may be identical or different, are chosen from hydrogen atoms, acyl radicals, carboxamido radicals, $C_1$–$C_4$ alkyl radicals optionally substituted with at least one radical chosen from hydroxyl, $C_1$–$C_4$ alkoxy, sulphino, $(C_1$–$C_4)$alkylsulphonyl, alkylsulphonamido, carboxyl, carboxamido, alkylsulphoxide, amino, mono- and $di(C_1$–$C_4)$alkylamino, and $C_2$–$C_4$ (poly)hydroxyalkylamino radicals;

$R_{11}$ and $R_{12}$ may also form with the nitrogen atom carrying them a 5- to 8-membered ring optionally substituted with at least one entity chosen from halogen atoms, hydroxyl, $C_1$–$C_4$ alkoxy, carboxyl, carbamyl, $(C_1$–$C_4)$alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals.

17. The nitro intermediate compound of formula:

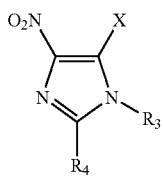

wherein:
$R_4$ is chosen from
a hydrogen atom;
phenyl radicals optionally substituted with at least one entity chosen from halogens and hydroxyl, $C_1$–$C_4$ alkoxy, carboxyl, carboxamido, $(C_1$–$C_4)$alkylsulphonyl, sulphonic, alkylsulphoxide, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals;

linear and branched $C_1$–$C_8$ alkyl radicals optionally substituted with at least one radical chosen from hydroxyl, $C_1$–$C_2$ alkoxy, carboxyl, carboxamido, $(C_1$–$C_4)$alkylsulphonyl, sulphonic, alkylsulphoxide, alkylsulphonamido and $NR_{13}R_{14}$ radicals, $NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals, 5- and 6-membered aromatic heterocycles optionally substituted with at least one entity chosen from hydroxyl, $C_1$–$C_2$ alkoxy, amino, dimethylamino, 2-hydroxyethylamino, bis(2-hydroxyethyl)amino radicals and chlorine atoms, $R_3$ is chosen from
$(C_1$–$C_4)$alkylsulphonyl radicals;

phenyl radicals and 5- and 6-membered aromatic heterocycles, wherein these radicals are optionally substituted with at least one entity chosen from halogens, hydroxyl, $C_1$–$C_4$ alkoxy, carboxyl, carboxamido, $(C_1$–$C_4)$alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals;

$R_{10}$ is chosen from $C_1$–$C_4$ alkyl radicals optionally substituted with at least one radical chosen from hydroxyl, $C_1$–$C_2$ alkoxy, amino, $(di)(C_1$–$C_4)$alkylamino and $C_2$–$C_4$ (poly)hydroxyalkylamino radicals, $R_{11}$, $R_{12}$, $R_{13}$, $R_{14}$, which may be identical or different, are chosen from hydrogen atoms, acyl radicals, carboxamido radicals, $C_1$–$C_4$ alkyl radicals optionally substituted with at least one radical chosen from hydroxyl, $C_1$–$C_4$ alkoxy, sulphino, $(C_1$–$C_4)$alkylsulphonyl, alkylsulphonamido, carboxyl, carboxamido, alkylsulphoxide, amino, mono- and $di(C_1$–$C_4)$alkylamino, and $C_2$–$C_4$ (poly)hydroxyalkylamino radicals;

$R_{11}$ and $R_{12}$ may also form with the nitrogen atom carrying them a 5- to 8-membered ring optionally substituted with at least one entity chosen from halogen atoms, hydroxyl, $C_1$–$C_4$ alkoxy, carboxyl, carbamyl, $(C_1$–$C_4)$alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, $(C_1$–$C_4)$alkylsulphonyl, sulphonic, alkylsulphoxide, alkylsulphonamido and $NR_{13}R_{14}$ radicals, X is chosen from a hydrogen atom; halogens; $C_1$–$C_4$ alkoxy radicals; phenoxy radicals optionally substituted with at least one entity chosen from halogen atoms, hydroxyl, $C_1$–$C_4$ alkoxy, carboxyl, $C_1$–$C_4$ alkoxycarbonyl, carboxamido, sulphino, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals; $C_1$–$C_4$ thioether radicals optionally substituted with at least one radical chosen from hydroxyl, $C_1$–$C_2$ alkoxy, carboxyl, and sulphonic radicals.

18. A dyeing composition comprising, in an appropriate dyeing medium:
   at least one oxidation base, and
   at least one coupler of the imidazole type of formula (I) and the addition salts thereof with an acid or a base:

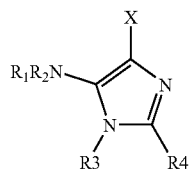

(I)

wherein:
$R_1$, $R_2$ and $R_4$, which may be identical or different, are chosen from
   hydrogen atoms;
   phenyl radicals optionally substituted with at least one entity chosen from halogens and hydroxyl, $C_1$–$C_4$ alkoxy, carboxyl, carboxamido, ($C_1$–$C_4$)alkylsulphonyl, sulphonic, alkylsulphoxide, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$)alkylsulphonyl, sulphonic, alkylsulphoxide, alkylsulphonamido and $NR_{13}R_{14}$ radicals;
   linear and branched $C_1$–$C_8$ alkyl radicals optionally substituted with at least one radical chosen from hydroxyl, $C_1$–$C_2$ alkoxy, carboxyl, carboxamido, ($C_1$–$C_4$)alkylsulphonyl, sulphonic, alkylsulphoxide, alkylsulphonamido and $NR_{13}R_{14}$ radicals,
$R_4$ may also be chosen from:
   $NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals,
   5- and 6-membered aromatic heterocycles optionally substituted with at least one entity chosen from hydroxyl, $C_1$–$C_2$ alkoxy, amino, dimethylamino, 2-hydroxyethylamino, bis(2-hydroxyethyl)amino radicals and chlorine atoms,
$R_1$ and $R_2$ may form with the nitrogen atom to which they are attached a 5- to 8-membered heterocycle in which at least one carbon atom of the carbon ring may be replaced by an entity chosen from oxygen, nitrogen and sulphur atoms and $SO_2$ groups; the carbon atoms of the ring may be substituted with a radical $R_5$; and with the proviso that the ring does not comprise a peroxide bond, or diazo or nitroso radicals;
$R_5$ is chosen from:
   halogen atoms;
   $C_1$–$C_4$ alkyl radicals optionally substituted with at least one radical chosen from hydroxyl, carboxyl, $C_1$–$C_4$ alkoxycarbonyl, $C_1$–$C_4$ alkoxy and $NR_6R_7$ radicals;
   carboxyl radicals;
   carboxamido radicals;
   ($C_1$–$C_4$)alkylsulphonyl radicals;
   alkylsulphonamido radicals;
   hydroxyl radicals;
   $C_1$–$C_4$ alkoxy radicals;
   $C_2$–$C_4$ hydroxyalkoxy radicals;
   aminosulphonyl radicals;
   $C_1$–$C_4$ thioether radicals;
   ($C_1$–$C_4$)alkylsulphoxide radicals;
   ($C_1$–$C_4$)alkylsulphonyl radicals;
   a radical $NR_8R_9$;
$R_3$ is chosen from
   a hydrogen atom;
   ($C_1$–$C_4$)alkylsulphonyl radicals;
   linear and branched $C_1$–$C_8$ alkyl radicals substituted with at least one radical chosen from hydroxyl, $OR_{10}$, carboxyl, carboxamido, ($C_1$–$C_4$)alkylsulphonyl, sulphonic, ($C_1$–$C_4$)alkylsulphoxide, alkylsulphonamido and $NR_{11}R_{12}$ radicals;
   phenyl radicals and 5- and 6-membered aromatic heterocycles, wherein these radicals are optionally substituted with at least one entity chosen from halogens, hydroxyl, $C_1$–$C_4$ alkoxy, carboxyl, carboxamido, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$) alkylsulphonyl, sulphonic, alkylsulphoxide, alkylsulphonamido and $NR_{13}R_{14}$ radicals;
$R_{10}$ is chosen from $C_1$–$C_4$ alkyl radicals optionally substituted with at least one radical chosen from hydroxyl, $C_1$–$C_2$ alkoxy, amino, (di)($C_1$–$C_4$)alkylamino and $C_2$–$C_4$ (poly)hydroxyalkylamino radicals,
$R_6$, $R_7$, $R_8$, $R_9$, $R_{11}$, $R_{12}$, $R_{13}$, $R_{14}$, which may be identical or different, are chosen from hydrogen atoms, acyl radicals, carboxamido radicals, $C_1$–$C_4$ alkyl radicals optionally substituted with at least one radical chosen from hydroxyl, $C_1$–$C_4$ alkoxy, sulphino, ($C_1$–$C_4$)alkylsulphonyl, alkylsulphonamido, carboxyl, carboxamido, alkylsulphoxide, amino, mono- and di($C_1$–$C_4$)alkylamino, and $C_2$–$C_4$ (poly)hydroxyalkylamino radicals;
$R_{11}$ and $R_{12}$ may also form with the nitrogen atom carrying them a 5- to 8-membered ring optionally substituted with at least one entity chosen from halogen atoms, hydroxyl, $C_1$–$C_4$ alkoxy, carboxyl, carbamyl, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$)alkylsulphonyl, sulphonic, alkylsulphoxide, alkylsulphonamido and $NR_{13}R_{14}$ radicals,
X is chosen from hydrogen atoms; halogens; $C_1$–$C_4$ alkoxy radicals; phenoxy radicals optionally substituted with at least one entity chosen from halogen atoms, hydroxyl, $C_1$–$C_4$ alkoxy, carboxyl, $C_1$–$C_4$ alkoxycarbonyl, carboxamido, sulphino, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals; $C_1$–$C_4$ thioether radicals optionally substituted with at least one radical chosen from hydroxyl, $C_1$–$C_2$ alkoxy, carboxyl, and sulphonic radicals.

19. The composition according to claim 18, wherein the at least one oxidation base is chosen from para-phenylenediamines, bisphenylalkylenediamines, para-aminophenols, ortho-aminophenols, heterocyclic bases and the addition salts thereof.

20. The composition according to claim 18, wherein the at least one oxidation base is present in an amount ranging from 0.001 to 10% by weight, relative to the total weight of the dyeing composition.

21. The composition according to claim 18, comprising at least one additional coupler chosen from meta-phenylenediamines, meta-aminophenols, meta-diphenols, naphthalene couplers, heterocyclic couplers other than those of formula (I), and the addition salts thereof.

22. The composition according to claim 18, wherein the at least one coupler is present in an amount ranging from 0.001 to 10% by weight, relative to the total weight of the dyeing composition.

23. The composition according to claim 16, comprising a cosmetically acceptable medium appropriate for dyeing keratinous fibers.

24. A dyeing composition according to claim 18, wherein $R_3$ is chosen from hydrogen atoms, alkyl radicals, hydroxyalkyl radicals, alkylsulphonyl radicals and phenyl radicals.

25. A dyeing composition according to claim 18, wherein said at least one coupler of the imidazole type of formula (I) is chosen from:
 5-aminoimidazole,
 5-amino-2-methylimidazole,
 5-amino-2-phenylimidazole,
 5-amino-N-methylimidazole,
 5-amino-2-methyl-N-methylimidazole,
 5-amino-2-phenyl-N-methylimidazole,
 5-amino-N-(2-hydroxyeth-1-yl)imidazole,
 5-amino-2-methyl-N-(2-hydroxyeth-1-yl)imidazole,
 5-amino-2-phenyl-N-(2-hydroxyeth-1-yl)imidazole,
 5-amino-N-(phenyl)imidazole,
 5-amino-2-methyl-N-(phenyl)imidazole,
 5-amino-2-phenyl-N-(phenyl)imidazole,
 5-methylaminoimidazole,
 5-methylamino-2-methylimidazole,
 5-methylamino-2-phenylimidazole,
 5-methylamino-N-methylimidazole,
 5-methylamino-2-methyl-N-methylimidazole,
 5-methylamino-2-phenyl-N-methylimidazole,
 5-methylamino-N-(2-hydroxyeth-1-yl)imidazole,
 5-methylamino-2-methyl-N-(2-hydroxyeth-1-yl)imidazole,
 5-methylamino-2-phenyl-N-(2-hydroxyeth-1-yl)imidazole,
 5-methylamino-N-(phenyl)imidazole,
 5-methylamino-2-methyl-N-(phenyl)imidazole,
 5-methylamino-2-phenyl-N-(phenyl)imidazole,
 5-dimethylaminoimidazole,
 5-dimethylamino-2-methylimidazole,
 5-dimethylamino-2-phenylimidazole,
 5-dimethylamino-N-methylimidazole,
 5-dimethylamino-2-methyl-N-methylimidazole,
 5-dimethylamino-2-phenyl-N-methylimidazole,
 5-dimethylamino-N-(2-hydroxyeth-1-yl)imidazole,
 5-dimethylamino-2-methyl-N-(2-hydroxyeth-1-yl)imidazole,
 5-dimethylamino-2-phenyl-N-(2-hydroxyeth-1-yl)imidazole,
 5-dimethylamino-N-(phenyl)imidazole,
 5-dimethylamino-2-methyl-N-(phenyl)imidazole,
 5-dimethylamino-2-phenyl-N-(phenyl)imidazole,
 5-(pyrrolidin-1-yl)imidazole,
 5-(pyrrolidin-1-yl)-2-methylimidazole,
 5-(pyrrolidin-1-yl)-2-phenylimidazole,
 5-(pyrrolidin-1-yl)-N-methylimidazole,
 5-(pyrrolidin-1-yl)-2-methyl-N-methylimidazole,
 5-(pyrrolidin-1-yl)-2-phenyl-N-methylimidazole,
 5-(pyrrolidin-1-yl)-N-(2-hydroxyeth-1-yl)imidazole,
 5-(pyrrolidin-1-yl)-2-methyl-N-(2-hydroxyeth-1-yl)imidazole,
 5-(pyrrolidin-1-yl)-2-phenyl-N-(2-hydroxyeth-1-yl)imidazole,
 5-(pyrrolidin-1-yl)-N-(phenyl)imidazole,
 5-(pyrrolidin-1-yl)-2-methyl-N-(phenyl)imidazole,
 5-(pyrrolidin-1-yl)-2-phenyl-N-(phenyl)imidazole,
 5-(3-hydroxypyrrolidin-1-yl)imidazole,
 5-(3-hydroxypyrrolidin-1-yl)-2-methylimidazole,
 5-(3-hydroxypyrrolidin-1-yl)-2-phenylimidazole,
 5-(3-hydroxypyrrolidin-1-yl)-N-methylimidazole,
 5-(3-hydroxypyrrolidin-1-yl)-2-methyl-N-methylimidazole,
 5-(3-hydroxypyrrolidin-1-yl)-2-phenyl-N-methylimidazole,
 5-(3-hydroxypyrrolidin-1-yl)-N-(2-hydroxyeth-1-yl)imidazole,
 5-(3-hydroxypyrrolidin-1-yl)-2-methyl-N-(2-hydroxyeth-1-yl)imidazole,
 5-(3-hydroxypyrrolidin-1-yl)-2-phenyl-N-(2-hydroxyeth-1-yl)imidazole,
 5-(3-hydroxypyrrolidin-1-yl)-N-(phenyl)imidazole,
 5-(3-hydroxypyrrolidin-1-yl)-2-methyl-N-(phenyl)imidazole,
 5-(3-hydroxypyrrolidin-1-yl)-2-phenyl-N-(phenyl)imidazole,
 5-(piperidin-1-yl)imidazole,
 5-(piperidin-1-yl)-2-methylimidazole,
 5-(piperidin-1-yl)-2-phenylimidazole,
 5-(piperidin-1-yl)-N-methylimidazole,
 5-(piperidin-1-yl)-2-methyl-N-methylimidazole,
 5-(piperidin-1-yl)-2-phenyl-N-methylimidazole,
 5-(piperidin-1-yl)-N-(2-hydroxyeth-1-yl)imidazole,
 5-(piperidin-1-yl)-2-methyl-N-(2-hydroxyeth-1-yl)imidazole,
 5-(piperidin-1-yl)-2-phenyl-N-(2-hydroxyeth-1-yl)imidazole,
 5-(piperidin-1-yl)-N-(phenyl)imidazole,
 5-(piperidin-1-yl)-2-methyl-N-(phenyl)imidazole,
 5-(piperidin-1-yl)-2-phenyl-N-(phenyl)imidazole,
 5-(2-hydroxyethyl)aminoimidazole,
 5-(2-hydroxyethyl)amino-2-methylimidazole,
 5-(2-hydroxyethyl)amino-2-phenylimidazole,
 5-(2-hydroxyethyl)amino-N-methylimidazole,
 5-(2-hydroxyethyl)amino-2-methyl-N-methylimidazole,
 5-(2-hydroxyethyl)amino-2-phenyl-N-methylimidazole,
 5-(2-hydroxyethyl)amino-N-(2-hydroxyeth-1-yl)imidazole,
 5-(2-hydroxyethyl)amino-2-methyl-N-(2-hydroxyeth-1-yl)imidazole,
 5-(2-hydroxyethyl)amino-2-phenyl-N-(2-hydroxyeth-1-yl)imidazole,
 5-(2-hydroxyethyl)amino-N-(phenyl)imidazole,
 5-(2-hydroxyethyl)amino-2-methyl-N-(phenyl)imidazole,
 5-(2-hydroxyethyl)amino-2-phenyl-N-(phenyl)imidazole,
 5-amino-4-chloroimidazole,
 5-amino-2-methyl-4-chloroimidazole,
 5-amino-2-phenyl-4-chloroimidazole,
 5-amino-N-methyl-4-chloroimidazole,
 5-amino-2-methyl-N-methyl-4-chloroimidazole, 5-amino-2-phenyl-N-methyl-4-chloroimidazole,
5-amino-N-(2-hydroxyeth-1-yl)-4-chloroimidazole,
5-amino-2-methyl-N-(2-hydroxyeth-1-yl)-4-chloroimidazole,
5-amino-2-phenyl-N-(2-hydroxyeth-1-yl)-4-chloroimidazole,
5-amino-N-(phenyl)-4-chloroimidazole,
5-amino-2-methyl-N-(phenyl)-4-chloroimidazole,
5-amino-2-phenyl-N-(phenyl)-4-chloroimidazole,
5-methylamino-4-chloroimidazole,
5-methylamino-2-methyl-4-chloroimidazole,
5-methylamino-2-phenyl-4-chloroimidazole,
5-methylamino-N-methyl-4-chloroimidazole,
5-methylamino-2-methyl-N-methyl-4-chloroimidazole,
5-methylamino-2-phenyl-N-methyl-4-chloroimidazole,
5-methylamino-N-(2-hydroxyeth-1-yl)-4-chloroimidazole,
5-methylamino-2-methyl-N-(2-hydroxyeth-1-yl)-4-chloroimidazole,
5-methylamino-2-phenyl-N-(2-hydroxyeth-1-yl)-4-chloroimidazole,
5-methylamino-N-(phenyl)-4-chloroimidazole,
5-methylamino-2-methyl-N-(phenyl)-4-chloroimidazole,
5-methylamino-2-phenyl-N-(phenyl)-4-chloroimidazole,
5-dimethylamino-4-chloroimidazole,
5-dimethylamino-2-methyl-4-chloroimidazole,
5-dimethylamino-2-phenyl-4-chloroimidazole,
5-dimethylamino-N-methyl-4-chloroimidazole,
5-dimethylamino-2-methyl-N-methyl-4-chloroimidazole,
5-dimethylamino-2-phenyl-N-methyl-4-chloroimidazole,
5-dimethylamino-N-(2-hydroxyeth-1-yl)-4-chloroimidazole,
5-dimethylamino-2-methyl-N-(2-hydroxyeth-1-yl)-4-chloroimidazole,
5-dimethylamino-2-phenyl-N-(2-hydroxyeth-1-yl)-4-chloroimidazole,
5-dimethylamino-N-(phenyl)-4-chloroimidazole,
5-dimethylamino-2-methyl-N-(phenyl)-4-chloroimidazole,
5-dimethylamino-2-phenyl-N-(phenyl)-4-chloroimidazole,
5-(pyrrolidin-1-yl)-4-chloroimidazole,
5-(pyrrolidin-1-yl)-2-methyl-4-chloroimidazole,
5-(pyrrolidin-1-yl)-2-phenyl-4-chloroimidazole,
5-(pyrrolidin-1-yl)-N-methyl-4-chloroimidazole,
5-(pyrrolidin-1-yl)-2-methyl-N-methyl-4-chloroimidazole,
5-(pyrrolidin-1-yl)-2-phenyl-N-methyl-4-chloroimidazole,
5-(pyrrolidin-1-yl)-N-(2-hydroxyeth-1-yl)-4-chloroimidazole,
5-(pyrrolidin-1-yl)-2-methyl-N-(2-hydroxyeth-1-yl)-4-chloroimidazole,
5-(pyrrolidin-1-yl)-2-phenyl-N-(2-hydroxyeth-1-yl)-4-chloroimidazole,
5-(pyrrolidin-1-yl)-N-(phenyl)-4-chloroimidazole,
5-(pyrrolidin-1-yl)-2-methyl-N-(phenyl)-4-chloroimidazole,
5-(pyrrolidin-1-yl)-2-phenyl-N-(phenyl)-4-chloroimidazole,
5-(3-hydroxypyrrolidin-1-yl)-4-chloroimidazole,
5-(3-hydroxypyrrolidin-1-yl)-2-methyl-4-chloroimidazole,
5-(3-hydroxypyrrolidin-1-yl)-2-phenyl-4-chloroimidazole,
5-(3-hydroxypyrrolidin-1-yl)-N-methyl-4-chloroimidazole,
5-(3-hydroxypyrrolidin-1-yl)-2-methyl-N-methyl-4-chloroimidazole,
5-(3-hydroxypyrrolidin-1-yl)-2-phenyl-N-methyl-4-chloroimidazole,
5-(3-hydroxypyrrolidin-1-yl)-N-(2-hydroxyeth-1-yl)-4-chloroimidazole,
5-(3-hydroxypyrrolidin-1-yl)-2-methyl-N-(2-hydroxyeth-1-yl)-4-chloroimidazole,
5-(3-hydroxypyrrolidin-1-yl)-2-phenyl-N-(2-hydroxyeth-1-yl)-4-chloroimidazole,
5-(3-hydroxypyrrolidin-1-yl)-N-(phenyl)-4-chloroimidazole,
5-(3-hydroxypyrrolidin-1-yl)-2-methyl-N-(phenyl)-4-chloroimidazole,
5-(3-hydroxypyrrolidin-1-yl)-2-phenyl-N-(phenyl)-4-chloroimidazole,
5-(piperidin-1-yl)-4-chloroimidazole,
5-(piperidin-1-yl)-2-methyl-4-chloroimidazole,
5-(piperidin-1-yl)-2-phenyl-4-chloroimidazole,
5-(piperidin-1-yl)-N-methyl-4-chloroimidazole,
5-(piperidin-1-yl)-2-methyl-N-methyl-4-chloroimidazole,
5-(piperidin-1-yl)-2-phenyl-N-methyl-4-chloroimidazole,
5-(piperidin-1-yl)-N-(2-hydroxyeth-1-yl)-4-chloroimidazole,
5-(piperidin-1-yl)-2-methyl-N-(2-hydroxyeth-1-yl)-4-chloroimidazole,
5-(piperidin-1-yl)-2-phenyl-N-(2-hydroxyeth-1-yl)-4-chloroimidazole,
5-(piperidin-1-yl)-N-(phenyl)-4-chloroimidazole,
5-(piperidin-1-yl)-2-methyl-N-(phenyl)-4-chloroimidazole,
5-(piperidin-1-yl)-2-phenyl-N-(phenyl)-4-chloroimidazole,
5-(2-hydroxyethyl)amino-4-chloroimidazole,
5-(2-hydroxyethyl)amino-2-methyl-4-chloroimidazole,
5-(2-hydroxyethyl)amino-2-phenyl-4-chloroimidazole,
5-(2-hydroxyethyl)amino-N-methyl-4-chloroimidazole,
5-(2-hydroxyethyl)amino-2-methyl-N-methyl-4-chloroimidazole,
5-(2-hydroxyethyl)amino-2-phenyl-N-methyl-4-chloroimidazole,
5-(2-hydroxyethyl)amino-N-(2-hydroxyeth-1-yl)-4-chloroimidazole,
5-(2-hydroxyethyl)amino-2-methyl-N-(2-hydroxyeth-1-yl)-4-chloroimidazole,
5-(2-hydroxyethyl)amino-2-phenyl-N-(2-hydroxyeth-1-yl)-4-chloroimidazole,
5-(2-hydroxyethyl)amino-N-(phenyl)-4-chloroimidazole,
5-(2-hydroxyethyl)amino-2-methyl-N-(phenyl)-4-chloroimidazole,
5-(2-hydroxyethyl)amino-2-phenyl-N-(phenyl)-4-chloroimidazole,
and the addition salts thereof with an acid or a base.

26. A dyeing composition according to claim 18, wherein said at least one coupler of the imidazole type of formula (I) is chosen from:
5-amino-2-methylimidazole;
5-amino-2-methyl-(2,3-dihydroxypropyl)imidazole;
5-amino-1,2-dimethylimidazole;
5-amino-1-(2-hydroxy)ethyl-2-methylimidazole;
2-(5-amino-2-methylimidazol-1-yl)ethyl ester of benzoic acid;
2-(5-amino-2-methylimidazol-4-ylsulphanyl)acetamide
and the addition salts thereof with an acid or a base.

27. A process for oxidation dyeing keratinous fibers, comprising applying to the fibers, in the presence of at least one oxidizing agent, for a period of time sufficient to develop the desired color, a dye composition comprising a compound of the imidazole type of formula (I) and the addition salts thereof with an acid or a base:

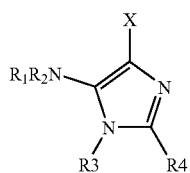

wherein:
- $R_1$, $R_2$ and $R_4$, which may be identical or different, are chosen from
  - hydrogen atoms;
  - phenyl radicals optionally substituted with at least one entity chosen from halogens and hydroxyl, $C_1$–$C_4$ alkoxy, carboxyl, carboxamido, ($C_1$–$C_4$)alkylsulphonyl, sulphonic, alkylsulphoxide, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$)alkylsulphonyl, sulphonic, alkylsulphoxide, alkylsulphonamido and $NR_{13}R_{14}$ radicals;
  - linear and branched $C_1$–$C_8$ alkyl radicals optionally substituted with at least one radical chosen from hydroxyl, $C_1$–$C_2$ alkoxy, carboxyl, carboxamido, ($C_1$–$C_4$)alkylsulphonyl, sulphonic, alkylsulphoxide, alkylsulphonamido and $NR_{13}R_{14}$ radicals,
- $R_4$ may also be chosen from:
  - $NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals,
  - 5- and 6-membered aromatic heterocycles optionally substituted with at least one entity chosen from hydroxyl, $C_1$–$C_2$ alkoxy, amino, dimethylamino, 2-hydroxyethylamino, bis(2-hydroxyethyl)amino radicals and chlorine atoms,
- $R_1$ and $R_2$ may form with the nitrogen atom to which they are attached a 5- to 8-membered heterocycle in which at least one carbon atom of the carbon ring may be replaced by an entity chosen from oxygen, nitrogen and sulphur atoms and $SO_2$ groups; the carbon atoms of the ring may be substituted with a radical $R_5$; and with the proviso that the ring does not comprise a peroxide bond, or diazo or nitroso radicals;
- $R_5$ is chosen from:
  - halogen atoms;
  - $C_1$–$C_4$ alkyl radicals optionally substituted with at least one radical chosen from hydroxyl, carboxyl, $C_1$–$C_4$ alkoxycarbonyl, $C_1$–$C_4$ alkoxy and $NR_6R_7$ radicals;
  - carboxyl radicals;
  - carboxamido radicals;
  - ($C_1$–$C_4$)alkylsulphonyl radicals;
  - alkylsulphonamido radicals;
  - hydroxyl radicals;
  - $C_1$–$C_4$ alkoxy radicals;
  - $C_2$–$C_4$ hydroxyalkoxy radicals;
  - aminosulphonyl radicals;
  - $C_1$–$C_4$ thioether radicals;
  - ($C_1$–$C_4$)alkylsulphoxide radicals;
  - ($C_1$–$C_4$)alkylsulphonyl radicals;
  - a radical $NR_8R_9$;
- $R_3$ is chosen from
  - a hydrogen atom;
  - ($C_1$–$C_4$)alkylsulphonyl radicals;
  - linear and branched $C_1$–$C_8$ alkyl radicals substituted with at least one radical chosen from hydroxyl, $OR_{10}$, carboxyl, carboxamido, ($C_1$–$C_4$)alkylsulphonyl, sulphonic, ($C_1$–$C_4$)alkylsulphoxide, alkylsulphonamido and $NR_{11}R_{12}$ radicals;
  - phenyl radicals and 5- and 6-membered aromatic heterocycles, wherein these radicals are optionally substituted with at least one entity chosen from halogens, hydroxyl, $C_1$–$C_4$ alkoxy, carboxyl, carboxamido, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$) alkylsulphonyl, sulphonic, alkylsulphoxide, alkylsulphonamido and $NR_{13}R_{14}$ radicals;
- $R_{10}$ is chosen from $C_1$–$C_4$ alkyl radicals optionally substituted with at least one radical chosen from hydroxyl, $C_1$–$C_2$ alkoxy, amino, (di)($C_1$–$C_4$)alkylamino and $C_2$–$C_4$ (poly)hydroxyalkylamino radicals,
- $R_6$, $R_7$, $R_8$, $R_9$, $R_{11}$, $R_{12}$, $R_{13}$, $R_{14}$, which may be identical or different, are chosen from hydrogen atoms, acyl radicals, carboxamido radicals, $C_1$–$C_4$ alkyl radicals optionally substituted with at least one radical chosen from hydroxyl, $C_1$–$C_4$ alkoxy, sulphino, ($C_1$–$C_4$)alkylsulphonyl, alkylsulphonamido, carboxyl, carboxamido, alkylsulphoxide, amino, mono- and di($C_1$–$C_4$)alkylamino, and $C_2$–$C_4$ (poly)hydroxyalkylamino radicals;
- $R_{11}$ and $R_{12}$ may also form with the nitrogen atom carrying them a 5- to 8-membered ring optionally substituted with at least one entity chosen from halogen atoms, hydroxyl, $C_1$–$C_4$ alkoxy, carboxyl, carbamyl, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$)alkylsulphonyl, sulphonic, alkylsulphoxide, alkylsulphonamido and $NR_{13}R_{14}$ radicals,
- X is chosen from a hydrogen atom; halogens; $C_1$–$C_4$ alkoxy radicals; phenoxy radicals optionally substituted with at least one entity chosen from halogen atoms, hydroxyl, $C_1$–$C_4$ alkoxy, carboxyl, $C_1$–$C_4$ alkoxycarbonyl, carboxamido, sulphino, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals; $C_1$–$C_4$ thioether radicals optionally substituted with at least one radical chosen from hydroxyl, $C_1$–$C_2$ alkoxy, carboxyl, and sulphonic radicals.

28. The process according to claim 27, wherein the at least one oxidizing agent is chosen from hydrogen peroxide, urea peroxide, alkali metal bromates, persalts, peracids and oxidase enzymes.

29. The process according to claim 27, wherein the at least one oxidizing agent is comprised within an oxidizing composition, which is applied to the fibers simultaneously with, or sequentially to, the dyeing composition.

30. A multicompartment kit, comprising
at least one first dye compartment comprising a dye composition comprising a compound of the imidazole type of formula (I) and the addition salts thereof with an acid or a base:

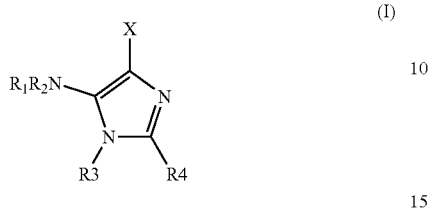

wherein:
$R_1$, $R_2$ and $R_4$, which may be identical or different, are chosen from
hydrogen atoms; p2 phenyl radicals optionally substituted with at least one entity chosen from halogens and hydroxyl, $C_1$–$C_4$ alkoxy, carboxyl, carboxamido, ($C_1$–$C_4$)alkylsulphonyl, sulphonic, alkylsulphoxide, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$)alkylsulphonyl, sulphonic, alkylsulphoxide, alkylsulphonamido and $NR_{13}R_{14}$ radicals;
linear and branched $C_1$–$C_8$ alkyl radicals optionally substituted with at least one radical chosen from hydroxyl, $C_1$–$C_2$ alkoxy, carboxyl, carboxamido, ($C_1$–$C_4$)alkylsulphonyl, sulphonic, alkylsulphoxide, alkylsulphonamido and $NR_{13}R_{14}$ radicals,
$R_4$ may also be chosen from:
$NR_{22}R_{23}$ radicals wherein $R_{22}$ and $R_{23}$, which may be identical or different, are chosen from hydrogen atoms, acyl radicals, $C_1$–$C_2$ alkyl radicals optionally substituted with a radical chosen from hydroxyl and $C_1$–$C_2$ alkoxy radicals,
5- and 6-membered aromatic heterocycles optionally substituted with at least one entity chosen from hydroxyl, $C_1$–$C_2$ alkoxy, amino, dimethylamino, 2-hydroxyethylamino, bis(2-hydroxyethyl)amino radicals and chlorine atoms,
$R_1$ and $R_2$ may form with the nitrogen atom to which they are attached a 5- to 8-membered heterocycle in which at least one carbon atom of the carbon ring may be replaced by an entity chosen from oxygen, nitrogen and sulphur atoms and $SO_2$ groups; the carbon atoms of the ring may be substituted with a radical $R_5$; and with the proviso that the ring does not comprise a peroxide bond, or diazo or nitroso radicals;
$R_5$ is chosen from:
halogen atoms;
$C_1$–$C_4$ alkyl radicals optionally substituted with at least one radical chosen from hydroxyl, carboxyl, $C_1$–$C_4$ alkoxycarbonyl, $C_1$–$C_4$ alkoxy and $NR_6R_7$ radicals;
carboxyl radicals;
carboxamido radicals;
($C_1$–$C_4$)alkylsulphonyl radicals;
alkylsulphonamido radicals;
hydroxyl radicals;
$C_1$–$C_4$ alkoxy radicals;
$C_2$–$C_4$ hydroxyalkoxy radicals;
aminosulphonyl radicals;
$C_1$–$C_4$ thioether radicals;
($C_1$–$C_4$)alkylsulphoxide radicals;
($C_1$–$C_4$)alkylsulphonyl radicals;
a radical $NR_8R_9$;
$R_3$ is chosen from
a hydrogen atom;
($C_1$–$C_4$)alkylsulphonyl radicals;
linear and branched $C_1$–$C_8$ alkyl radicals substituted with at least one radical chosen from hydroxyl, $OR_{10}$, carboxyl, carboxamido, ($C_1$–$C_4$)alkylsulphonyl, sulphonic, ($C_1$–$C_4$)alkylsulphoxide, alkylsulphonamido and $NR_{11}R_{12}$ radicals;
phenyl radicals and 5- and 6-membered aromatic heterocycles, wherein these radicals are optionally substituted with at least one entity chosen from halogens, hydroxyl, $C_1$–$C_4$ alkoxy, carboxyl, carboxamido, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$) alkylsulphonyl, sulphonic, alkylsulphoxide, alkylsulphonamido and $NR_{13}R_{14}$ radicals;
$R_{10}$ is chosen from $C_1$–$C_4$ alkyl radicals optionally substituted with at least one radical chosen from hydroxyl, $C_1$–$C_2$ alkoxy, amino, (di)($C_1$–$C_4$)alkylamino and $C_2$–$C_4$ (poly)hydroxyalkylamino radicals,
$R_6$, $R_7$, $R_8$, $R_9$, $R_{11}$, $R_{12}$, $R_{13}$, $R_{14}$, which may be identical or different, are chosen from hydrogen atoms, acyl radicals, carboxamido radicals, $C_1$–$C_4$ alkyl radicals optionally substituted with at least one radical chosen from hydroxyl, $C_1$–$C_4$ alkoxy, sulphino, ($C_1$–$C_4$)alkylsulphonyl, alkylsulphonamido, carboxyl, carboxamido, alkylsulphoxide, amino, mono- and di($C_1$–$C_4$)alkylamino, and $C_2$–$C_4$ (poly)hydroxyalkylamino radicals;
$R_{11}$ and $R_{12}$ may also form with the nitrogen atom carrying them a 5- to 8-membered ring optionally substituted with at least one entity chosen from halogen atoms, hydroxyl, $C_1$–$C_4$ alkoxy, carboxyl, carbamyl, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals, wherein the $C_1$–$C_4$ alkyl radicals are optionally substituted with at least one radical chosen from hydroxyl, $C_1$–$C_4$ alkoxy, carboxyl, carboxamido, ($C_1$–$C_4$)alkylsulphonyl, sulphonic, alkylsulphoxide, alkylsulphonamido and $NR_{13}R_{14}$ radicals,
X is chosen from a hydrogen atom; halogens; $C_1$–$C_4$ alkoxy radicals; phenoxy radicals optionally substituted with at least one entity chosen from halogen atoms, hydroxyl, $C_1$–$C_4$ alkoxy, carboxyl, $C_1$–$C_4$ alkoxycarbonyl, carboxamido, sulphino, ($C_1$–$C_4$)alkylsulphonyl, sulphonic, alkylsulphoxide, $C_1$–$C_4$ thioether, alkylsulphonamido, $NR_{13}R_{14}$, and $C_1$–$C_4$ alkyl radicals; $C_1$–$C_4$ thioether radicals optionally substituted with at least one radical chosen from hydroxyl, $C_1$–$C_2$ alkoxy, carboxyl, and sulphonic radicals;
at least one second compartment comprising at least one oxidizing agent.

* * * * *

UNITED STATES PATENT AND TRADEMARK OFFICE
CERTIFICATE OF CORRECTION

PATENT NO. : 7,238,212 B2
APPLICATION NO. : 10/857919
DATED : July 3, 2007
INVENTOR(S) : Jacqueline Mavro et al.

It is certified that error appears in the above-identified patent and that said Letters Patent is hereby corrected as shown below:

Col. 29, line 22, "alkylsuiphonyl" should read -- alkylsulphonyl --.

Col. 35, line 19, delete "p2" and start new paragraph.

Signed and Sealed this

Eighteenth Day of September, 2007

JON W. DUDAS
*Director of the United States Patent and Trademark Office*